(12) United States Patent
Hamer

(10) Patent No.: US 8,349,586 B1
(45) Date of Patent: Jan. 8, 2013

(54) **COMMENSAL STRAIN OF *E. COLI* ENCODING AN HIV GP41 PROTEIN**

(75) Inventor: Dean Hamer, Washington, DC (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 68 days.

(21) Appl. No.: 11/710,512

(22) Filed: Feb. 26, 2007

Related U.S. Application Data

(63) Continuation-in-part of application No. PCT/US2005/030216, filed on Aug. 25, 2005.

(60) Provisional application No. 60/604,051, filed on Aug. 25, 2004, provisional application No. 60/688,376, filed on Jun. 8, 2005.

(51) Int. Cl.
*C12P 1/00* (2006.01)
*C12P 21/06* (2006.01)

(52) U.S. Cl. ........................ 435/41; 424/93.21

(58) Field of Classification Search ............ 435/41, 435/69.1; 424/93.21
See application file for complete search history.

(56) References Cited

U.S. PATENT DOCUMENTS

| | | | |
|---|---|---|---|
| 5,356,797 A * | 10/1994 | Niesel et al. ............... | 435/69.3 |
| 5,705,160 A | 1/1998 | Bruce et al. | |
| 5,733,540 A | 3/1998 | Lee | |
| 5,804,179 A | 9/1998 | Bruce et al. | |
| 5,821,081 A | 10/1998 | Boyd et al. | |
| 6,140,114 A * | 10/2000 | Klatzmann et al. ........ | 435/320.1 |
| 6,180,100 B1 | 1/2001 | Bruce et al. | |
| 6,277,370 B1 | 8/2001 | Cavaliere Ved. Vesely et al. | |
| 6,365,156 B1 | 4/2002 | Lee | |
| 6,605,286 B2 | 8/2003 | Steidler et al. | |
| 2003/0086020 A1 | 5/2003 | Gai et al. | |
| 2003/0228297 A1 | 12/2003 | Chang et al. | |

FOREIGN PATENT DOCUMENTS

| WO | WO 96/11277 | | 4/1996 |
|---|---|---|---|
| WO | WO 9611708 A1 | * | 4/1996 |
| WO | WO 02/081655 | * | 10/2002 |

OTHER PUBLICATIONS

Gentschev (TRENDS in microbiology, Jan. 2002, vol. 10, No. 1, p. 39-45).*
Tapadar (Abstracts of the General Meeting of Am. Soc. for Mcirobiol., 2002, vol. 102, p. 184).*
Beliayskaia (Molekuliarnaia genetika, mkrobiologiia i virusologiia, Nov.-Dec. 1994, No. 6, p. 12-6, abstract only).*
Eckert (Ann. Rev. Biochem., 2001, vol. 70, p. 777-810).*
Gentschev (Gene, 1996, vol. 179, p. 133-140).*
Mollenkopf (Appl Microbiol Biotechnol, 1996, vol. 45, p. 629-637).*
Spreng (Mol. Microbiol., 1999, vol. 31, p. 1596-1598).*
Liu (Current Pharmaceutical Design, 2004, vol. 10, p. 1827-1843).*
Lodinova-Zadnikova (Biology of the Neonate, 1997, vol. 71, No. 4, p. 224-232).*
Cukrowska (Scand. J. Immunol. 2002, vol. 55, p. 204-209).*
Blight (Trends in biotech., Nov. 1994, vol. 12, No. 11, p. 450455).*
Su, Micorbial Pathogenesis, 1992, vol. 13, p. 465-476.*
Buddenborg, International J. Medical Microbiol., Jan. 2008, vol. 298, No. 1-2, p. 105-114.*
Hormaeche, Ce and Khan, CMA. (1996) Recombinant bacteria as vaccine carriers of heterologous antigens. In Concepts in Vaccine Development, (Kaufmann. S.H.E.. ed.) pp. 327-349.*
Stricker (Medical Hypotheses, Jun. 1997, vol. 48, p. 527-9).*
Bangham (Lancet, Nov. 29, 1997, vol. 350, p. 1617-1621).*
Korth (Virology, 1998, vol. 247, p. 265-273).*
Hanke (Immunology Letters, 1999, vol. 66, p. 177-181).*
Veljkovic (Vaccine, 2001, vol. 19, p. 1855-1862).*
Weber (Eur. J. Clin. Microbiol. Infect. Dis., Nov. 2001, vol. 20, p. 800-803).*
Ready (Nature Medicine, Apr. 2003, vol. 9, No. 4, p. 376).*
Lori (Current Medical and Chemical Anti-Infective Agents, 2004, vol. 3, p. 31-41).*
Dong (J. Exp. Med., Dec. 20, 2004, vol. 200, No. 12, p. 1547-1557).*
Cohen (Science, Jul. 1, 2005, vol. 309, p. 99).*
Pitisuttithum Punnee (Curr HIV Res, Jan. 2005, vol. 3 (1), p. 17-30).*
Burgers (Best practice & research. Clinical obstetrics & gynaecology, Apr. 2005, vol. 19, No. 2, p. 277-91).*
Kirby (Nature Med. 1998, vol. 4, p. 1302-1307).*
DeNoon (Aidsweekly plus, Nov. 23, 1998).*
Borchardt (New from The Scientist, 2001, vol. 2, No. 1, 20010801-04).*
Champagne (J. Biol. Chem. Feb. 2009, vol. 284, No. 6, p. 3619-3627).*
Lalezari (New England J. Med. May 29, 2003, vol. 348, No. 22, p. 2175-2185).*
Dorland's Medical Dictionary definition of "microbicide", 2010.*
Beliayskaia (Molekuliarnaia genetika, mikrobiologiia i virusologiia, Nov.-Dec. 1994, No. 6, p. 12-16).*
Encyclo Online Encyclopedia definition of Vaccine, 2010.*
Root (PNAS, 2003, vol. 100, p. 5016-5021).* Sweet (Methods in Molecular Biology,2003, vol. 235, p. 277-288).*
International Search Report.
Rao et al., "*Toward a live microbial microbicide for HIV: Commensal bacterial secreting an HIV fusion inhibitor peptide*", PNAS, 2005, 102(34), pp. 11993-11998.
Chang et al., "*Inhibition of HIV infectivity by a natural human isolate of Lactobacillus jensenii engineered to express functional two-domain CD4*", PNAS, 2003, 100(20), pp. 11672-11677.
Giomarelli et al., "*The microbicide cyanovirin-N expressed on the surface of commensal bacterium Streptococcus gordinii captures HIV-1*", AIDS, 2002, 16(10), pp. 1351-1356.
Beninati et al., "*Therapy of mucosal candidiasis by expression of an anti-idiotype in human commensal bacteria*", Nature Biotechnology, 2000, 18(10), pp. 1060-1064.
Krüger et al., "*In situ delivery of passive immunity by lactobacilli producing single-chain antibodies*", Nature Biotechnoloogy, 2002, 20(7), pp. 702-702.
Kruis at al., "*Maintaining remission of ulcerative colitis with the probiotic Escherichia coli Nissle 1917 is as effective as with standard mesalazine*", GUT, 2004, 53(11), pp. 1617-1623.

(Continued)

Primary Examiner — Michael C. Wilson
(74) *Attorney, Agent, or Firm* — Sheridan Ross P.C.

(57) ABSTRACT

The present invention relates, e.g., to a commensal bacterium which can colonize the genitourinary and/or gastrointestinal mucosa, and which, under suitable conditions, secretes a heterologous antimicrobial polypeptide, wherein the secreted antimicrobial polypeptide is effective to inhibit infectivity by, or a pathogenic activity of, a pathogen. In a most preferred embodiment, the antimicrobial polypeptide inhibits HIV infection (e.g., fusion) and/or pathogenesis. Also described are preventive or therapeutic compositions comprising the commensal bacteria, and methods to inhibit infectivity and/or pathogenesis, using the bacteria.

13 Claims, 5 Drawing Sheets

OTHER PUBLICATIONS

Rembacken et al., "*Non-pathogenic Escherichia coli versus mesalazine for the treatment of ulcerative colitis: a randomised trial*", Lancet, 1999, 354(9179), pp. 635-639.

Tromm et al., "*The Probiotic E. coli Strain Nissle 1917 for the Treatment of Collagenous Colitis: First Results of an Open-Label Trial*," Z Gastroenterol, 2004, 42(5), pp. 365-369.

Tzschaschel et al., "*An Escherichia coli hemolysin transport system-based vector for the export of polypeptides: Export of Shiga-like toxin IleB subunit by Salmonella typhimurium aorA*", Nature Biotechnology, 1996, 14, pp. 765-769.

Fernandez et al., "*Specific Secretion of Active Single-Chain Fv Antibodies into the Supernatants of Escherichia coli Cultures by Use of the Hemolysin System*," Applied and Environmental Microbiology, 2000, 66(11), pp. 5024-5029.

Eckert et al., "*Mechanisms of Viral Membrane Fusion and Its Inhibition*," Annu. Rev. Biochem., 2001, 70, pp. 777-810.

Hockertz, S., "*Augmentation of host defence against bacterial and fungal infectios of mice pretreated with the non-pathogenic Escherichia coli strain Nissle 1917*", Arzneimittelforschung, 1997, 47(6), pp. 793-796 (Abstract only).

Kruis, W., "*Review article: antibiotics and probiotics in inflammatory bowel disease*", Ailment Phqarmacol Ther. 2004, 20 Suppl. 4:75-8 (Abstract Only).

Kilby et al., "*The Safety, Plasma Pharmacokinetics, and Antiviral Activity of Subcutaneous Enfuvirtide (T-20), a Peptide Inhibitor of gp41-Mediated Virus Fusion, in HIV-Infected Adults*," AIDS Research and Human Retroviruses, 2002, 18(10), pp. 685-693.

Andersen, "*Channel-tunnels: outer membrane components of type 1 secretion systems and multidrug efflux pumps of Gram-negative bacteria*," Rev Physiol Biochem Pharmacol, 2003, 147, pp. 122-165.

Gentschev et al., "*The E-coli α-hemolysin secretion system and ifs use in vaccine development*," Trends in Microbiology, 2002, 10(1), pp. 39-45.

Liu et al., "*Engineered Vaginal Lactobacillus Strain for Mucosal Delivery of the Human Immunodeficiency Virus Inhibitor Cyanovirin-N*", Antimicrobial Agents and Chemotherapy, 2006, 50(10), pp. 3250-3259.

Lee et al., "*Multimerization Potential of the Cytoplasmic Domain of the Human Immunodeficiency Virus Type 1 Transmembrane Glycoprotein gp41*", J. Bio. Chem., 2000, 275(21), pp. 15809-15819.

Eckert at al., "*Design of potent inhibitors of HIV-1 entry from the gp41 N-peptide region*," PNAS, 2001, 98(20), pp. 11187-11192.

Louis et al., "*Covalent Trimers of the Internal N-terminal Trimeric Coiled-coil of gp41 and Antibodies Directed against Them are Potent Inhibitors of HIV Envelope-mediated Cell Fusion*", J. Bio. Chem., 2003, 278(22), pp. 20278-20285.

\* cited by examiner

○ MuLV-gfp + Etag-HlyA$_{218}$
✱ MuLV-gfp + HIV$_{CS2}$-HlyA$_{218}$
△ HIV-gfp + Etag-HlyA$_{218}$
▽ HIV-gfp + HIV$_{CS2}$-HlyA$_{218}$
□ HIV-gfp + HIV$_{CS2}$-HlyA$_{103}$
◇ HIV-gfp + HIV$_{CS2}$-HlyA$_{53}$

US 8,349,586 B1

COMMENSAL STRAIN OF *E. COLI* ENCODING AN HIV GP41 PROTEIN

This application is a Continuation-In-Part of PCT application, PCT/US2005/030216, filed Aug. 25, 2005, and claims the benefit of the filing date of U.S. provisional applications, Ser. No. 60/604,051, filed Aug. 25, 2004 and 60/688,376, filed Jun. 8, 2005, both of which are incorporated herein in their entirety.

FIELD OF THE INVENTION

The present invention relates, e.g., to a commensal bacterium that can colonize the mucosa of the gastrointestinal and/or genitourinary tract and, under suitable conditions, can block the infectious and/or disease-causing activity of a pathogen by secreting a heterologous antimicrobial polypeptide. Also described are preventive and therapeutic compositions comprising such bacteria, and methods to inhibit a pathogen, comprising administering such a bacterium to a subject in need of such treatment.

BACKGROUND INFORMATION

The global HIV/AIDS epidemic continues to grow at an alarming rate. There are now more than 40 million people infected with HIV, most of whom will die in the next decade, and last year alone there were 5 million new infections. Most HIV transmission worldwide is through unprotected vaginal intercourse. Unprotected anal intercourse, another high risk activity, is also practiced globally by both homosexual and heterosexual individuals. Ingestion of HIV-containing breast milk by infants is a third common route of infection.

Attempts to slow the spread of HIV by behavioral measures have had little success, and no widely available biomedical intervention is available. The development of a safe and effective vaccine has proven to be extraordinarily difficult. Topical vaginal and anal microbicides are a promising alternative to vaccines because they can in principle be formulated from already-known HIV inhibitors such as reverse transcriptase inhibitors or monoclonal antibodies. However, they suffer the same fundamental problem as condoms: they have to be used each time people have sex.

A new approach is urgently needed. The present application describes an approach in which benign, commensal bacteria that can colonize mucosa of human beings are genetically engineered to secrete anti-HIV polypeptides, which then inhibit HIV infection and/or pathogenesis. The approach can also be used to genetically engineer commensal bacteria to inhibit a variety of pathogens other than HIV; e.g., other viruses, pathogenic bacteria, fungi and parasites.

DESCRIPTION OF THE DRAWINGS

FIG. 1 diagrams the structure of some antimicrobial polypeptides and the use of the hemolysin system to obtain their secretion.

FIG. 2 is a gel which shows secretion and biological activity of HIV fusion inhibitor peptides from bacteria.

FIG. 3 shows the colonization of the mouse gastrointestinal and genitourinary tract by genetically modified *E. coli* Nissle 1917. Female mice, strain CD1, were administered 5×10$^8$ *E. coli* Nissle 1917::C52-HlyA208::HlyB HlyD, either orally or rectally. The mice were either treated with no antibiotic, pretreated for one day prior to inoculation with antibiotic, or both pre-treated and continuously post-treated with antibiotic.

FIG. 4 shows the colonization and tissue distribution of anti-HIV bacteria in Rhesus Macaque.

FIG. 5 shows a Macaque Protection Experiment. Experimental Macaques were inoculated with a mixture of *E. coli* Nissle 1917 expressing a mixture of antiviral peptides, as indicated in Example II, and were challenged rectally with the challenge virus SHIV162p3 at a high dose (100% infection of control animals).

DESCRIPTION OF THE INVENTION

Figure 1A:
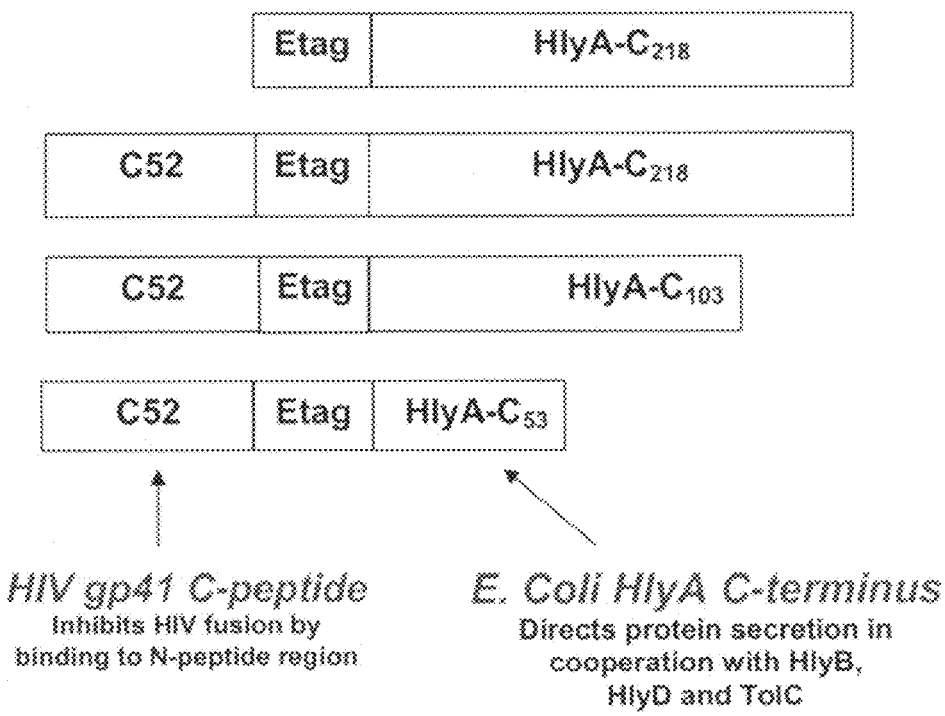
FIG. 1A is a scheme of recombinant DNA constructs used to express the control peptide Etag-HlyA218 and the HIV fusion inhibitor peptides C52-HlyA218, C52-HlyA103, and C52-HlyA53. C52 is a peptide derived from the C-terminal region of HIV gp41; Etag is a linker sequence containing a common epitope; and HlyA is the carboxy-terminal secretion signal sequence of *E. coli* hemolysin A.

The present invention relates, e.g., to a commensal bacterium that can colonize genitourinary and/or gastrointestinal mucosa, and that, under suitable conditions, secretes an antimicrobial polypeptide that inhibits the infectiousness and/or pathogenicity of a pathogen. The commensal bacterium can be, for example, a non-pathogenic strain of a gram negative bacterium, such as *E. coli*; or the pathogen can be, for example, a virus, bacterium, fungus or parasite.

In preferred embodiments of the invention, HIV infection and/or pathogenesis is inhibited. Commensal microorganisms of the invention (e.g., genetically modified *E. coli*) can colonize the genitourinary and/or gastrointestinal mucosa, which are the major sites of HIV transmission through vaginal and anal intercourse and breast feeding, and are normally coated by a biofilm of commensal microorganisms. By using strains that can compete with the preexisting vaginal, intestinal and oral microflora, these genetically engineered bacteria can persistently colonize the mucosa, and can serve as a continuous source of secreted antimicrobial polypeptide. The secreted polypeptide can, e.g., prevent HIV infection directly by binding to the virus or indirectly by binding to cellular receptors and/or co-receptors for the virus. The microorganism secreting the polypeptide is self-sustaining and even transmissible from person to person. The methods of the invention can be used to prevent new infections, or to inhibit viral rebound in infected and antiretroviral-treated individuals when HAART (Highly Active Anti-Retroviral Therapy) is stopped or becomes ineffective due to drug resistance.

Among the advantages of the methods of the present invention are that they are inexpensive and easy to administer in resource-poor settings, and require one or infrequent rather than daily applications. The protective microbes have the potential to be spread by sexual and casual contact as well as by deliberate administration. Perhaps most important, HIV has no opportunity to evolve evasive measures—unlike the case for traditional vaccines.

One aspect of the invention is a commensal, gram negative bacterium which can colonize genitourinary and/or gastrointestinal mucosa and which, under suitable conditions, secretes a recombinant antimicrobial polypeptide, wherein the secreted antimicrobial peptide is effective to inhibit infection by, and/or a pathogenic activity of, a pathogen. In embodiments of the invention, the gram negative bacterium is *Bacteriodes melaminogenicus, Bacteriodes vulgatus, Bacteriodes fragilis, Pseudomonas aeruginosa, Veillonella parvula*, or a *fusobacterium*. In a preferred embodiment, the commensal, gram negative bacterium is a strain of *E. coli*, most preferably the strain Nissle 1917. The antimicrobial polypeptide in these gram negative bacteria is fused in phase to a secretion signal, preferably a carboxyterminal secretion signal of the hemolysin A gene.

Another aspect of the invention is a commensal bacterium which can colonize genitourinary and/or gastrointestinal mucosa, and which, under suitable conditions, secretes a recombinant, antimicrobial polypeptide; wherein the secreted antimicrobial polypeptide is effective to inhibit infectivity by, and/or a pathogenic activity of a pathogen; provided that the commensal bacterium is not a commensal *Lactobacillus* or *Streptococcus* (e.g. a readily transformable strain of one of those bacteria). In embodiments of this aspect of the invention, the bacterium is either gram positive or gram negative. For example, the bacterium may be a commensal strain of *E. coli, Bacillus, Lactococcus, Bitodobacterium, Bacteriodes*, or *Neisseria*.

Any of the above types of bacteria is sometimes referred to herein as a "commensal bacterium of the invention." It will be evident from context which type of bacterium is being discussed.

In embodiments of the invention, the commensal bacterium can colonize genitourinary mucosa and/or gastrointestinal mucosa. In embodiments of the invention, the antimicrobial polypeptide is directed against a virus (e.g., HIV, SHIV and/or SIV, preferably HIV), bacterium, fungus or parasite. For example, an antimicrobial polypeptide directed against HIV may comprise a functional inhibitory fragment from the C-terminal region of an HIV, SHIV or SIV gp41 protein (such as a functional fragment that consists essentially of about 20 to about 200 amino acids, preferably about 47 amino acids or about 20 amino acids, from the C-terminal region of gp41); or a functional inhibitory fragment comprising amino acids from the N-terminal region of gp41 from HIV-1, HIV-2 or SIV; an allosteric site on gp120; a predicted extracellular loop of CCR5; a single strand anti CD4 antibody; a mini-protein mimetic of CD4; an alpha-defensin or theta-defensin; a CD38 sequence homologous to the V3 loop of gp120; polphemusin II, which antagonizes CXCR4; a RANTES peptide that binds to CCR5; or a HIV surface binding peptide such as cyanovirin. In preferred embodiments, the secretion signal is a secretion-effective C-terminal fragment of HlyA; and/or the expression control sequence comprises a constitutive promoter (e.g., the expression control sequence comprises a promoter from the *E. coli* lac operon and a translational control sequence from bacteriophage T7). In one embodiment, the bacterium comprises, stably integrated into its chromosome, sequences encoding an antimicrobial polypeptide fused in frame to a secretory signal, wherein the coding sequences are operably linked to an expression control sequence.

Another aspect of the invention is a pharmaceutical composition, comprising an effective amount of a commensal bacterium of the invention and a pharmaceutically acceptable carrier.

Another aspect of the invention is a method for making a gram negative, commensal bacterium which can colonize genitourinary and/or gastrointestinal mucosa, and which, under suitable conditions, secretes a recombinant, antimicrobial polypeptide, wherein the secreted antimicrobial polypeptide is effective to inhibit infection by, or a pathogenic activity of, a pathogen. The method comprises introducing into a gram negative commensal bacterium that can colonize genitourinary and/or gastrointestinal mucosa a polynucleotide that encodes a heterologous antimicrobial polypeptide fused in phase to a secretion signal (e.g. a secretion signal from the C-terminal region of HlyA), wherein the coding sequences for the antimicrobial polypeptide and the fused secretion signal are operably linked to an expression control sequence. In a preferred embodiment, the polynucleotide is stably introduced into the bacterium.

Another aspect of the invention is a method for inhibiting HIV infectivity and/or pathogenicity, comprising contacting the HIV with an effective amount of a commensal bacterium of the invention, under conditions in which the secreted antimicrobial polypeptide is effective to inhibit HIV infectivity and/or pathogenicity.

Another aspect of the invention is a method for inhibiting HIV infectivity and/or pathogenicity in a subject in need of such treatment, comprising administering to the subject an effective amount of a commensal bacterium of the invention, under conditions in which the secreted anti-microbial polypeptide is effective to inhibit HIV infectivity and/or pathogenicity. In preferred embodiments of the invention, the commensal bacterium is administered orally, intrarectally, or intravaginally.

Another aspect of the invention is a method for providing a source of an antimicrobial polypeptide at a genitourinary and/or gastrointestinal mucosum in a subject in need of such treatment, comprising administering to the subject an effective amount of a commensal bacterium of the invention, under conditions effective for the bacterium to colonize the mucosum and to express and secrete an effective amount of the antimicrobial polypeptide. In general, the antimicrobial polypeptide is present in an amount sufficient to be detected in a sample collected from the mucosal surface.

Another aspect of the invention is a kit for delivering an effective dose of an antimicrobial agent to a genitourinary and/or gastrointestinal mucosum, comprising an effective amount of a commensal bacterium of the invention, in a pharmaceutically acceptable solution.

Another aspect of the invention is a vector comprising a polypeptide as described in FIG. 1A.

As used herein, a "commensal" bacterium is one that is symbiotic with its host (e.g. a human host), is non-pathogenic, and can occupy the genitourinary and/or gastrointestinal tracts but does not invade other areas of the body such as the blood, lungs, or heart. Among the microorganisms which can colonize gastrointestinal and/or genitourinary mucosa are microorganisms which naturally inhabit those mucosa, or microorganisms which have been manipulated (e.g., adapted) so that they can colonize the mucosa. Exemplary methods for adapting such microorganisms are discussed below. A microorganism that can "colonize" a mucosum is one that can compete with the preexisting microflora and take up residence in the mucosum. As used herein, "gastrointestinal mucosa" include the linings of, e.g., the rectum, colon, cecum and upper intestine (jejunum, duodenum and ileum) as well as the oral cavity and larynx (which are normally considered part of the upper respiratory tract, but are herein referred to as components of the gastrointestinal tract because they are the gateway to this portion of the anatomy). "Genitourinary mucosa" include the lining of, e.g., the cervix, vagina, penis, and urinary tract. Many organisms that can colonize gastrointestinal mucosa are also able to colonize genitourinary mucosa, and vice-versa. For example, the majority of *E. coli* strains isolated from vaginal samples of normal healthy women were also found in their own stool samples (Foxman et al. (2002) *Am J Epidemiol* 156, 1133-40).

A "mucosal membrane" or a "mucosal surface" refers to a tissue layer found lining various tubular cavities of the body such as the oropharynx, small intestine, large intestine, rectum, penis, vagina, mouth, uterus, etc. It is composed of a layer of epithelium containing numerous unicellular mucous glands and an underlying layer of areolar and lymphoid tissue, separated by a basement membrane. This membrane is typically colonized by a variety of bacteria even when the host is healthy.

Commensal bacteria of the invention may take any of a variety of forms. Preferably they are strains which exhibit favorable growth and colonization properties, and which can be efficiently (and, in some cases, stably) transformed with recombinant DNA constructs. By "favorable growth and colonization properties" is meant that the microorganism can efficiently colonize a mucosal lining and can continue to grow and/or remain attached to the mucosal lining to the extent necessary to secrete effective amounts of the antimicrobial polypeptide. In some cases the commensal bacterium is a genetically engineered version of a species that naturally inhabits the mucosum which is being colonized. In other cases it is a modified version of a strain that has been previously administered to humans as a probiotic and thereby known to be a good colonizer and non-pathogenic.

Humans are inhabited by over 1000 different species of bacteria which inhabit and/or can colonize normal healthy mucosa, and which can be used in methods of the invention (see, e.g., Guarner et al. (2003) *Lancet* 361, 512-9; Salminen et al. (1995) *Chemotherapy* 41 Suppl 1, 5-15; and Galask, R. P. (1988) *Am J Obstet Gynecol* 158, 993-5). Several specific examples of commensal bacteria are described below, but a skilled worker will recognize appropriate ways to modify any particular disclosure herein so as to be applicable to additional species, strains and isolates of bacteria. Bacteria can be used which naturally exhibit desired growth and colonization behavior. Alternatively, bacteria can be manipulated, using conventional procedures, to enhance their ability to colonize a mucosal surface. For example, a first method involves repetitively selecting for rapid colonizing bacteria on animal or human mucosal layers. For example, one applies a wild type bacterial strain to a mucosal surface and repetitively isolates and in vitro cultures bacteria, returning at each step to the mucosal surface. Ultimately, a bacterium with an enhanced colonizing ability is obtained. A second method involves expression of fusion proteins on the surface of recombinant bacteria. The fusion protein consists of a host-binding domain linked to a polypeptide of interest. The host-binding domain will allow the bacteria to bind to certain determinants (protein or carbohydrate) on a selected host mucosal surface with high affinity, thus conferring the bacteria a survival advantage over the resident microflora. In addition, one can use bacterial strains known to be non-pathogenic and efficient colonizers by virtue of their use as probiotics, which are live microorganisms which when administered in adequate amounts confer health benefits on the host. Typically, probiotic bacteria have demonstrated safety in human use, survival in the intestine, adhesion to mucosa, and at least temporary colonization of the gut. Some examples of suitable bacteria are described below.

*E. coli:*

*E. coli* is an almost universal member of the normal human intestinal and rectal microflora. It is the first species to colonize the gut in infants, and reaches concentrations from $10^9$ to $10^{12}$ CFU/gm feces in adults (Guarner et al. (2003) *Lancet* 361, 512-9; Salminen et al. (1995) *Chemotherapy* 41 Suppl 1, 5-15). *E. coli* is also frequently found in the vagina. Foxman et al. (2002), supra found *E. coli* in 28% of asymptomatic women, with the highest rate in sexually active individuals. It is therefore anticipated that expression of anti-HIV agents by *E. coli* will protect strongly against rectal transmission by anal intercourse, and very likely against vaginal transmission by vaginal intercourse and oral transmission by breast milk as well.

One preferred strain of *E. coli* is Nissle 1917, which was isolated in 1917 from the stool of a German soldier who, unlike his comrades, survived an outbreak of enterocolitis. This strain is widely used as a probiotic in Europe, where it is produced under the trade name of Mutoflor, to treat intestinal disorders including diarrhea, irritable bowel disease, ulcerative colitis and Crohn's disease. Nissle 1917 is an excellent colonizer of the human gut, both in adults who have undergone antibiotic therapy and in infants, and does not produce CNF toxin, hemolysin, P-fimbrae, or S-fimbrae (Altenhoefer et al. (2004) *FEMS Immunol Med Microbiol* 40, 223-9; Blum-Oehler et al. (2003) *Res Microbiol* 154, 59-66; Lodinova-Zadnikova et al. (1997) *Biol Neonate* 71, 224-32; Rembacken et al. (1999) Lancet 354, 635-9; Stentebjerg-Olesen et al. (1999) *J Bacteriol* 181, 7470-8; Blum et al. (1995) *Infection* 23, 234-6). As shown below, Nissle 1917 retains colonizing activity following genetic manipulation to produce anti-HIV peptides.

Other preferred strains of *E. coli* are those capable of growing both in the gastrointestinal and genitourinary tracts and of colonizing new hosts. For example, Foxman et al. (2002), supra described 57 strains of *E. coli* that appear to satisfy these criteria by virtue of having been isolated from both the feces and vaginal washes of normal health women and the feces of their male sexual partners.

Other Gram Negative Bacteria:

A number of gram negative bacteria besides *E. coli* inhabit the mucosal surfaces of interest. Such strains are especially suitable because they have the potential to secrete antimicrobial peptides through a gram negative type I secretion pathways such as the hemolysin pathway discussed herein. Some specific species suitable for this invention are *Bacteroides melaminogenicus, Bacteriodes vulgatus, Bacteriodes fragilis, Pseudomonas aeruginosa, Veillonella parvula*, and *fusobacteria*.

*Streptococcus:*

Another suitable bacterium is *Streptococcus*. A particularly preferable species is *Streptococcus gordonii*, which is capable of colonizing the human vagina, and which has been used to express a number of heterologous polypeptides (see, e.g., Beninati et al. (2000) *Nat Biotechnol* 18, 1060-4 and Giomarelli et al. (2002) *Aids* 16, 1351-6). Other suitable *Streptococcus* strains include *Streptococcus* sps, *S. mitis, S. oralis, S. salivalius*, and *S. pneumoniae*, all of which naturally inhibit and/or colonize at least the nasal/pharynx mucosa of healthy individuals.

*Lactobacillus:*

Another suitable bacterium is *Lactobacillus*, which is a major component of the human vaginal microflora. Any *Lactobacillus* isolate with favorable growth and colonization properties, and which can be transformed efficiently with heterologous DNA, is suitable for use in the present invention. A natural vaginal isolate of *Lactobacillus jensenii*—*Lactobacillus jensenii* strain 1153—that exhibits favorable growth and colonization properties has been identified by Chang et al. (2003) *Proc Natl Acad Sci U S A* 100, 11672-7. See also US Pat. Pub. 20030228297. Chang et al. report that this isolate can be used in conjunction with a *Lactococcus*-based plasmid to express and secrete foreign proteins and that, when engineered to express biologically active two-domain CD4, it inhibits HIV infectivity of susceptible cultured cell lines. This construct is unlikely to be clinically useful because of the relatively low expression levels and modest potency that were observed. However, other constructs expressed in this or in other suitable *Lactobacillus* isolates may be more suitable for clinical use. Other suitable *lactobacillus* strains include, e.g., *Lactobacillus* sps, *L. crispatus, L. fermentum, L. casei* (e.g., *L. casei* ss *rhamnosus, L. casei* ss *alactosus*), *L. salivarius, L. catenaforme, L. minutus, L. gasseri, L. acidophilus, L. plantarum*, and *L. brevis*.

Other suitable bacteria will be evident to the skilled worker. These include, e.g., *Lactococcus lactis*, which is a nonpathogenic gram positive bacterium frequently used to produce fermented foods, and which has been engineered to secrete interleukin-10 as a treatment for murine colitis (Steidler et al. (2000) *Science* 289, 1352-5) and *Bacillus*, which has been employed as a probiotic (Hoa et al. (2000) *Appl Environ Microbiol* 66, 5241-7). Other suitable bacteria include *Staphylococcus* sps, *S. epidermidis, S. aureus*, and *Neisseria* sps, all of which naturally inhabit at least the nasal/oral pharynx of healthy individuals; and *Corynebacterium* sps, which naturally inhabits vaginal mucosa. Furthermore, vectors are also available for *Bifodobacteria*, which are among the most common bacteria in the human intestine (van der Werf et al. (2001) *J Agric Food Chem* 49, 378-83).

A variety of antimicrobial polypeptides are encompassed by the invention. As used herein, the terms "polypeptide," "peptide," and "protein" are used interchangeably to refer to a polymer of amino acid residues. These terms as used herein encompass amino acid chains of any length, including full-length proteins, wherein the amino acid residues are linked by covalent bonds. A preferred length is from about 100 to 275 amino acids (approximately 13,500 to 37,125 daltons), which the inventor has shown to be sufficiently long to display potent antimicrobial activity, yet sufficiently short to permit efficient secretion into the surrounding environment (see Examples below).

An antimicrobial polypeptide of the invention can be used to prevent any step in pathogenesis, including, e.g., initial infection of a naive host by the pathogen; continuing reinfection of a chronically infected host by the pathogen; detrimental biochemical, physiological, and immunological effects caused by infection with the pathogen; and spread of the pathogen to other hosts.

The pathogens which can be inhibited by methods of the invention include, e.g., viruses, bacteria, fungi and parasites. The antimicrobial polypeptides of the invention can block these pathogens either directly by binding to them, or indirectly, e.g. by preventing their interaction with host cell components.

Examples of antimicrobial polypeptides that inhibit infection by directly binding to the pathogen include antibodies, antibody fragments, and single-chain antibodies that recognize an external protein of the pathogen, such as a viral envelope or cell membrane protein. Also included in this category are receptor or receptor domains that a viral or bacterial pathogen binds to infect a host, or a functional virus-binding fragment of the receptor. Such direct binding proteins can inhibit infection or pathogenicity by a variety of mechanisms. For example, they can act as decoys and block entry of the pathogen into the cell. Alternatively, the antimicrobial polypeptide can be an agent that binds to the pathogen and thereby, e.g., inhibits pathogen replication, viability, entry, etc. For example, since viruses require binding to a receptor on the target cell surface for infection, strategies directed at inhibiting the interaction of a virus with its host receptor are effective at preventing infection. In some embodiments, a polypeptide of the invention binds or inhibits sexually transmitted pathogens and other pathogens transmitted to or from the vagina or the rectum.

Examples of antimicrobial polypeptides that indirectly inhibit infection by preventing interactions of the pathogen with the host include antibodies, antibody fragments, single-chain antibodies, and ligands that bind to a cellular receptor and/or co-receptor for the pathogen.

In a preferred embodiment, the pathogen which is inhibited is a virus. Among the many viruses which can be inhibited by the methods of the invention are rotavirus, Norwalk agent, papillomavirus, adenovirus, respiratory syncytia virus, corona virus, cytomegalovirus, coxsackievirus, echovirus, hepatitis A virus, hepatitis B virus, hepatitis C virus, rhinovirus, human immunodeficiency virus, poliovirus and other picornaviruses, Epstein-Barr virus, influenza virus, parainfluenza virus, and herpes simplex virus.

The skilled worker will recognize a wide variety of suitable inhibitory polypeptides that inhibit viral entry into a host cell. For example, agents that bind to and inhibit virus surfaces or virus receptors on a host cell are known for Human Rhinovirus (major group ICAM-1), Influenza A (sialic acid), Adenovirus (vitronectin), Epstein-Barr Virus (CR2 (C3 receptor)), Herpes Simplex Virus type I (heparin sulfate/HveA/HveC), Herpes Simplex Virus type II (heparin sulfate/HveA/HveC), Poliovirus (Poliovirus Receptor (PVR)), and Hepatitis B (asialoglycoprotein). The inhibitors can be, e.g., functional fragments of the receptors which compete with the virus for entry into the cell. Alternatively, polypeptides can be used which bind to conserved determinants on viral capsids and thereby prevent or inhibit their binding to a receptor.

A "functional fragment" or an "active fragment," as used herein, refers to a fragment that retains at least one biological activity of the full-length molecule (e.g., the ability to bind to the pathogen or, in the case of HIV, to inhibit HIV fusion). A skilled worker will recognize how to generate suitable functional fragments of an antimicrobial polypeptide, e.g. based on known properties of the polypeptides. Some such fragments have been disclosed.

In a particularly preferred embodiment of the invention, the virus which is inhibited is human immunodeficiency virus (HIV), simian immunodeficiency virus (SIV), or a chimeric simian-human immunodeficiency virus (SHIV). "HIV," as used herein, refers to HIV-1, HIV-2, or any subset therein. Preferably, the virus inhibited by a method of the invention is HIV-1. In one embodiment, the antimicrobial polypeptide is a functional anti-HIV polypeptide derived from the C-terminal region of the gp41 Env protein of HIV (to inhibit HIV and SHIV) or SIV (to inhibit SIV). Preferably, the polypeptide consists essentially of about 20 to about 200 amino acids from this C-terminal region, more preferably about 47 amino acids or about 20 amino acids from this C-terminal region. "Consisting essentially of," when used in the context of polypeptides, refers to a sequence which is intermediate between the number of amino acid residues encompassed by the term "consisting of" and the longer length encompassed by the term "comprising." Residues in addition to the residues encompassed by "consisting of" language do not affect the basic and novel characteristics (e.g., in the case of a polypeptide of the invention, the ability to inhibit infectivity or pathogenicity of an organism) of the molecule encompassed by the "consisting of" language.

In one embodiment, the antimicrobial polypeptide is an amino acid fragment, that contains about 47 amino acids (e.g., about 40 to about 55 amino acids) from the C-terminal region of gp41 of HIV or SIV, together with additional amino acids that are added to allow cloning into an expression vector. In a preferred embodiment, the antimicrobial polypeptide is an amino acid fragment, henceforth termed "C52," that contains 47 amino acids from the C-terminal region of gp41 of HIV or SIV, together with an additional 5 amino acids that were added to allow cloning into the expression vector. See Root et al. (2003) *Proc Natl Acad Sci USA* 100, 5016-5021. The sequence of the HIV C52 peptide is MGGHTTWMEW-DREINNYTSLIHSLIEESQNQQEK NEQELLELDK-WASLWNWF (SEQ ID NO: 1) and the sequence of the SIV C52 peptide is MGGHTTWQEWERKVDFLEENITA LLEEAQIQQEKNMYELQKLNSWDVFGNWF (SEQ ID NO: 2). Without wishing to be bound by any particular mechanism, it is suggested that the C52 polypeptides inhibit HIV and SIV infection by binding to the N-terminal region of HIV and SIV gp41, thereby preventing the formation of the "trimer of hairpins" structure required for fusion of the virus to the host cell membrane (Eckert et al. (2001) *Annu Rev Biochem.* 70, 777-810).

The HIV and SIV C52 polypeptides have several notable advantages as viral inhibitors: they are potent; the sequences are highly conserved among different HIV isolates; the polypeptides do not require disulfide bonding or other post-translational modifications; similar peptides are active against both direct and trans infection of multiple primary cell types (Ketas et al., (2003) *J Virol* 77, 2762-7; Ketas et al. (2003) *AIDS Res Hum Retroviruses* 19, 177-86); and similar polypeptides, such as the closely related C-terminal peptide T-20 (enfuvirtide), are currently in clinical use as a salvage antiretroviral therapy (Kilby et al. (1998) *Nat Med* 4, 1302-7; Kilby et al. (2002) *AIDS Res Hum Retroviruses* 18, 685-93). As described below, the C52 polypeptides and all of the other antimicrobial polypeptides discussed herein are preferably covalently attached to additional sequences that allow detection of the heterologous polypeptides with antibodies (e.g., the E tag epitope) and/or that allow secretion (e.g., the hlyA C-terminal secretion signal; see below).

In addition to C52, several other polypeptides can inhibit the infectivity of HIV, SIV and SHIV by blocking virus-cell fusion. These include peptides from the N-terminal region of gp41 from HIV, SHIV or SIV, which are thought to inhibit viral fusion by targeting the C-terminal region of the fusion apparatus, especially when prevented from aggregation by attachment to a soluble helix-forming domain, (Eckert et al. (2001) *Proc Natl Acad Sci USA* 98, 11187-92; Louis et al. (2003) *J Biol Chem* 278(22), 20278-85); and peptides from the C-terminal region of gp41 from HIV-1, HIV-2 or SIV, which are thought to be the target of a 5-helix construct in which three N-terminal peptides and two C-terminal peptides from HIV are covalently linked (Root et al. (2001) *Science* 291, 884-8). Other combinations of C-terminal and N-terminal peptides from HIV, SIV and SHIV have similar effects. One such inhibitor is the potent fusion inhibitor, T1249, which comprises a mixture of sequences from the C-terminal region of gp41 of HIV-1, the C-terminal region of gp41 of HIV-2, and the C-terminal region of SIV. This peptide, which is described in U.S. Pat. No. 6,656,906 and Eron et al. (2004) *J Infect Dis* 189, 1075-83, appears to function by the same mechanism as the C52 peptides described herein. Typically, anti-HIV polypeptides of the invention are less than about 200 amino acids in length; longer and shorter polypeptides are included.

Various other peptides and short proteins that directly recognize HIV, SIV and SHIV can inhibit infection at different points in the viral life cycle. Short linear peptides that inhibit HIV infection by binding to an allosteric site on gp120 have been identified by phage display (Biorn et al. (2004) *Biochemistry*, 43, 1928-38). One such peptide is the peptide 12P1, which is discussed in Ferrer et al. (1999) *J Virol* 73, 5795-5812. The 2D-CD4 polypeptide, which contains the first approximately 183 amino acids of 2-domain CD4, binds to gp120 with the same affinity as the intact protein (Salzwedel et al. (2000) *J. Virol.* 74, 326-333). High affinity miniprotein mimetics of CD4 can also be isolated and used to inhibit HIV entry (see, e.g., Dowd et al. (2002) *Biochemistry* 41, 7038-46 and Li et al. (2001) *J Pept Res* 57, 507-18).

Other peptides can inhibit HIV, SIV and SHIV infection indirectly, by blocking cellular receptors and co-receptors. For example, derivatives of RANTES, which is a natural ligand for the CCR5 chemokine receptor, block infection by R5-tropic strains of HIV that utilize CCR5 as co-receptor (Simmons et al. (1997) *Science* 276, 276-9). Peptides corresponding to the predicted extracellular loops of CCR5 also inhibit infection by R5 strains of HIV, which are the type most frequently transmitted (Agrawal et al. (2004) *Blood* 103, 1211-7). CXCR4, the other major co-receptor for HIV, can be inhibited by peptides such as T22 (Masuda et al. (1992) *Biochem Biophys Res Commun.* 189, 845-50; D. Schols (2004) *Curr Top Med Chem* 4, 883-93.

Other suitable, well-known anti-HIV polypeptides will be evident to the skilled worker. These include, e.g., a miniprotein mimetic of CD4; an alpha-defensin or theta-defensin; a CD38 sequence homologous to the V3 loop of gp120; polphemusin II, which antagonizes CXCR4; and an HIV surface binding peptide, such as cyanovirin (Giomarelli et al. (2002) *Aids* 16), 1351-6, In another embodiment of the invention, the pathogen which is inhibited is a bacterium. Anti-bacterial polypeptides include those that bind to or inhibit growth or colonization by uropathogenic *E. coli*. Among the bacteria that can be inhibited by methods of the invention are bacteria which cause sexually transmitted diseases, including, e.g., *Neisseria gonorrhoeae* (gonorrhea), *Treponema palladium* (syphilis) and *Chlamydia trachomatis* (chlamydia). Exemplary anti-bacterial polypeptides include, e.g., permeability-increasing protein against gram-negative bacteria (Levy (2002) *Expert Opin. Investig. Drugs* 11, 159-167), mammalian anti-microbial peptides, β-defensins (Ganz et al, (1995) *Pharmacol. Ther.* 66, 191-205), bacteriocins (e.g., Loeffler et al. (2001) *Science* 294, 2170-2172) and antibodies that specifically bind to the bacteria. Agents that target bacterial cell walls are also included. In general, target specificity is determined by the C-terminal domain of these molecules (known as cell wall targeting sequences). The best studied of these are molecules which bind specifically to choline, which is a constituent of the cell wall of *Strep. pneumoniae* and a few other bacterial species (e.g., *S. oralis*). These molecules include LytA and PspA. Other bacteria-binding molecules include RIB, which targets *Listeria monocytogenes* and *Bacillus subtilis*, and Lysostaphin, which targets *Staph. aureus*. The C-terminal (targeting) domains of such molecules to can be used. Suitable inhibitory molecules include, e.g., LytA, a C-terminal binding domain of PspA, a C-terminal domain of lysostaphin ($SPA_{CWT}$), a C-terminal domain of InlB, an anti-S-layer protein antibody, and an anti-peptidoglycan antibody.

In another embodiment of the invention, the pathogen which is inhibited is a fungus. Anti-fungal polypeptides include those that bind to or inhibit growth or colonization by fungi such as *Candida*.

In another embodiment of the invention, the pathogen which is inhibited is a parasite. Suitable anti-parasite polypeptides will be evident to the skilled worker.

Another class of antimicrobial polypeptides, which are effective against viruses or other pathogens, comprises antibodies that are specific for a surface component of a pathogen, such as a virus, or for a cellular receptor or co-receptor involved in pathogen binding or entry into a host. The antibody can be, e.g. a single chain antibody, or an antibody fragment, such as an F(ab) or a F(ab')$_2$. For example, the anti-CD4 antibody 5A8, which allows HIV-CD4 interactions but blocks subsequent steps required for fusion, or active fragments thereof, can be used. This antibody is attractive for microbial expression because it potently neutralizes virtually all strains of HIV-1, and a humanized version has been shown to decrease viral loads and increase CD4 T cell counts in HIV-infected subjects in a phase I clinical trial (Kuritzkes et al. (2004) *J Infect Dis* 189, 286-91). Antibodies such as b12, and improved derivatives thereof, recognize the CD4 binding site of HIV Env protein with high potency (Kessler et al. (1997) *AIDS Res Hum Retroviruses* 13, 575-82; McHugh et al. (2002) *J Biol Chem* 277, 34383-90). An antibody "specific for" a polypeptide includes an antibody that recognizes a defined sequence of amino acids, or epitope, either present in the full length polypeptide or in a peptide fragment thereof. In one embodiment, the antibody is a neutralizing antibody. By "neutralizing" is meant herein that binding of an antibody to a pathogen or its receptor inhibits or prevents infection of the host by the pathogen.

Therapeutic polypeptides that are not antimicrobial polypeptides are also included in the invention. Such polypeptides, which are secreted by commensal microorganisms of the invention, include, among many others, anti-inflammatory molecules, growth factors, molecules that bind to, or antagonize, growth factors, therapeutic enzymes, antibodies (including, e.g., antibody fragments or single-chain antibodies) and molecules that inhibit or treat cancer including cervical cancer. Anti-inflammatory molecules include, e.g., antibodies or other molecules that specifically bind to tumor necrosis factor (TNF) or interleukin-8 (IL-8). Other exemplary anti-inflammatory molecules include IL-10 and IL-11. Growth factors useful in the invention include, e.g., those involved in local tissue repair such as keratinocyte growth factor (KGF), heparin-binding epidermal growth factor (HB-EGF), fibroblast growth factor (FGF) and transforming growth factor-beta (TGF-β), or antagonists of these molecules. Therapeutic enzymes include, e.g., nitric oxide (NO) synthase. Anti-cancer molecules include those that induce apoptosis, that regulate cell cycle such as p53, or that act as a vaccine to target cancer-specific epitopes.

Active fragments or variants of any of the antimicrobial polypeptides discussed herein are included in the invention, provided that the altered polypeptide retains at least one biological activity of the unaltered (e.g., wild type) polypeptide (e.g., the ability to inhibit infection by, or pathogenic activity of, a pathogen). The fragment or variant can have the sequence of a naturally occurring polypeptide (e.g., it can be a peptide fragment of a longer antimicrobial polypeptide), or it can have a variant of the sequence of a naturally occurring polypeptide. Suitable variants may comprise small deletions, insertions or substitutions compared to the wild type protein; preferably, the variant contains one or more conservative amino acid substitutions. The variants may be naturally occurring (e.g., allelic variants or strain differences), or they may be introduced artificially, using conventional methods. A skilled worker can readily determine if a given polypeptide, either wild type or variant, exhibits a desired antimicrobial activity.

Under suitable conditions, a commensal microorganism of the invention secretes an antimicrobial polypeptide, which is effective to inhibit infection by, or a pathogenic activity of, a pathogen. "Suitable conditions," as used herein, include the presence of regulatory elements (including secretion signals) that allow effective amounts of the polypeptide to be produced and secreted. "Suitable conditions" also include a physiological environment which is conducive to the expression and secretion of the polypeptide. Such conditions are found in the various mucosa to which the microorganisms are administered. For example, suitable conditions for expressing an inducible promoter include a physiological environment in which an agent is present that induces the promoter. Suitable conditions also include the presence of an amount of the microorganism that is sufficient to compete effectively with resident microorganisms and to colonize the mucosal surfaces of an infected individual, thereby allowing secretion of an effective amount of an antimicrobial polypeptide.

A commensal microorganism of the invention that secretes an antimicrobial polypeptide which is effective to inhibit infection by, or a pathogenic activity of, a pathogen, can generally produce and secrete a sufficient amount of the inhibitory peptide into the surrounding milieu (either into a cell culture medium in vitro or into a suitable locale in vivo) to inhibit a microbe (e.g. to inhibit growth of a virus) without the need to purify or concentrate the antimicrobial peptide further. For example, Example I demonstrates that an *E. coli* Nissle 1918 strain of bacteria engineered to secrete a $C_{52}$-hHly$_{218}$ peptide in vitro secretes the peptide into the broth to a concentration of 40 mg/l, which is 1.25 µM. The amount of this peptide known to be required to inactivate HIV is about 5 nM. Thus, this strain can secrete greater than 100-fold more peptide than is required to inactivate HIV. In embodiments of the invention, the effective amount of an antimicrobial polypeptide that is secreted is, e.g., greater than about 10-fold, 20-fold, 50-fold, 75-fold etc. of the amount known to be needed to inhibit infectivity by, and/or a pathogenic activity of, a pathogen.

The commensal organisms of the invention preferably secrete recombinant, antimicrobial polypeptides. These organisms comprise a polynucleotide which encodes a heterologous antimicrobial polypeptide fused in phase to a secretion signal, wherein the coding sequences are operably linked to an expression control sequence. The polynucleotide can have been introduced into the microorganism (or an ancestor thereof) by transfection, transformation, or the like.

Methods of making recombinant constructs, in which a sequence encoding a polypeptide of interest is operably linked to an expression control sequence, are conventional. In general, a sequence of interest is operably linked to an expression control sequence in an expression vector. A construct (a recombinant construct) generated in this manner can express the polypeptide when introduced into a cell.

Methods of making recombinant constructs, as well as many of the other molecular biological methods used in conjunction with the present invention, are discussed, e.g., in Sambrook, et al. (1989), *Molecular Cloning, a Laboratory Manual*, Cold Harbor Laboratory Press, Cold Spring Harbor, N.Y.; Ausubel et al. (1995). *Current Protocols in Molecular Biology*, N.Y., John Wiley & Sons; Davis et al. (1986), *Basic Methods in Molecular Biology*, Elseveir Sciences Publishing, Inc., New York; Hames et al. (1985), *Nucleic Acid Hybridization*, IL Press; Dracopoli et al. (current edition) *Current Protocols in Human Genetics*, John Wiley & Sons, Inc.; and Coligan et al. (current edition) *Current Protocols in Protein Science*, John Wiley & Sons, Inc.

As used herein, the term "expression control sequence" means a polynucleotide sequence that regulates expression of a polypeptide coded for by a polynucleotide to which it is functionally ("operably") linked. Expression can be regulated at the level of the mRNA or polypeptide. Thus, the term expression control sequence includes mRNA-related elements and protein-related elements. Such elements include promoters, domains within promoters, upstream elements, enhancers, ribosome binding sequences, transcriptional terminators, etc. An expression control sequence is operably linked to a nucleotide sequence (e.g., a coding sequence) when the expression control sequence is positioned in such a manner to effect or achieve expression of the coding sequence. For example, when a promoter is operably linked 5' to a coding sequence, expression of the coding sequence is driven by the promoter. Examples of promoters that can be used to drive expression in *E. coli* host bacteria include the trp, lac, tac, and T7 phage promoters (Melton et al. (1984) *Polynucleotide Res.* 12(18), 7035-7056; Dunn et al. (1984) *J. Mol. Biol.* 166, 477-435; U.S. Pat. No. 5,891,636; Studier et al., (1987) Gene Expression Technology, in *Methods in Enzymology*, 85, 60-89) and synthetically improved versions of these promoters such as those described in Liu et al. (2004) Proc Natl Acad Sci 101, 6911-6. In the case of translational signals, such as a ribosome binding sites, the control element is typically inserted in between the promoter and the start point of translation. Many potent *E. coli* translational control sequences are available from highly expressed chromosomal loci or from bacteriophage, such as bacteriophage T7.

In a preferred embodiment of the invention, the fusion polypeptide is expressed under the control of a constitutive promoter, e.g. a promoter from the *E. coli* lac operon, and a translational control sequence, e.g. from bacteriophage T7. When these elements are present in a high copy number plasmid, they lead to constitutive high level expression of the antimicrobial fusion polypeptide. Alternatively, promoters that are induced in the conditions in which the host bacteria colonizes the mucosa can be employed. For example, promoters that are active in the vagina, e.g. after the introduction of semen, have been described (see, e.g., U.S. Pat. No. 6,242,194). Promoters regulated by iron are activated in the gastrointestinal tract.

To promote secretion of an antimicrobial polypeptide of the invention, the polypeptide is preferably fused in phase to a suitable secretion signal. An especially preferred method of this invention uses the secretory apparatus of hemolysin in a gram negative bacterial host. A polypeptide of interest is fused to the carboxy-terminal secretion signal of the hemolysin A gene (hlyA). The Hly system specifically secretes target proteins from the bacterial cytoplasm into the extracellular medium without a periplasmic intermediate. This is one of very few gram negative bacterial systems that allow protein secretion into the culture medium, and has been extensively used in live vaccines (Andersen, C. (2003) *Rev Physiol Biochem Pharmacol* 147, 122-65; Gentschev et al. (2002) *Trends Microbiol* 10, 39-45). The protein machinery of the Hly type I secretory apparatus consists of two operon-specific inner membrane components, HlyB and HlyD, and the chromosomally encoded outer membrane protein, TolC, which form a protein channel between the inner and outer membranes. The HlyB-HlyD complex recognizes the carboxy-terminal portion of HlyA, thereby allowing the secretion of polypeptides fused to this signal sequence.

In a preferred method of this invention, a construct is generated which encodes a fusion polypeptide comprising an antimicrobial polypeptide of interest fused to the carboxyterminal about 50 to 250 amino acids of the HlyA gene from *E. coli* strain LE2001 (G ray et al. (1989) *J Cell Sci Suppl* 11, 45-57; Mackman et al. (1984) *Mol Gen Genet* 193, 312-5; Mackman et al. (1984) *Mol Gen Genet* 196, 129-34). This carboxyterminal region comprises a secretion signal. For example, as shown in the Examples herein, the construct may encode one of the following 218, 103 or 53 amino acid sequences from the carboxyterminal portion of the HlyA gene:

HlyA218

(SEQ ID NO: 3)
NSLAKNVLSGGKGNDKLYGSEGADLLDGGEGNDLLKGGYGNDIYRYLSG

YGHHIIDDEGGKDDKLSLADIDFRDVAFKREGNDLIMYKAEGNVLSIGH

KNGITFKNWFEKESDDLSNHQIEQIFDKDGRVITPDSLKKAFEYQQSNN

KVSYVYGHDASTYGSQDNLNPLINEISKIISAAGNFDVKEERSAASLLQ

LSGNASDFSYGRNSITLTASA;

HlyA103

(SEQ ID NO: 4)
LSNHQIEQIFDKDGRVITPDSLKKAFEYQQSNNKVSYVYGHDASTYGSQ

DNLNPLINEISKIISAAGNFDVKEERSAASLLQLSGNASDFSYGRNSIT

LTASA;

HlyA53

(SEQ ID NO:5)
LNPLINEISKIISAAGNFDVKEERSAASLLQLSGNASDFSYGRNSITLT

ASA

Preferably, the constructs are introduced into a bacterial cell on a high copy plasmid, or on a low copy number plasmid or chromosomal integration site in conjunction with a strong promoter. The HlyB and HlyD genes from *E. coli* LE2001 are preferably introduced into the bacterial cell as a single operon carried on a low copy number plasmid or integrated into a chromosomal site. Alternatively, the HlyB and HlyD genes can be introduced into the cell on two separate low copy number plasmids, or can be integrated independently into different chromosomal sites. The precise ratio of hlyA fusion polypeptide to hlyB and hlyD gene products is not critical. TolC protein is an endogenous gram negative bacterial protein and does not need to be artificially introduced into the bacteria. Example I illustrates the production of an anti-HIV polypeptide using the hlyA secretory system.

Additional suitable secretion signals will be evident to the skilled worker. For example, secretory signals that can be used for gram positive bacteria include secretion signals derived from the *Lactococcus lactis* S-protein, *Lactobacillus amylovorus* alpha-amylase, or *Streptococcus pyogenes* M6 protein genes. Some signal sequences that are suitable for use in lactobacilli are described in US Pat. Pub. 20030228297.

Methods to introduce constructs of the invention into bacterial cells will be evident to the skilled worker. The most common are chemical transformation, electroporation, and infection or transduction with a phage vector.

Recombinant polypeptides of the invention can be expressed, e.g., from a vector, such as a plasmid or phage, or from a stably integrated sequence. Plasmids are particularly useful for experimental procedures, such as those described in the Examples herein. In general, such a plasmid contains a selectable marker, such as resistance to an antibiotic, which is used to select for the plasmid and to maintain it in the cell. A large number of suitable selectable markers are known in the art, as are methods employing them. If desired, a plasmid bearing an antibiotic resistance gene can be introduced into a subject along with the antibiotic, in order to facilitate the establishment of the bacterium in the mucosum.

However, because antibiotic resistance markers might be transferred to opportunistic human pathogens such as *Staphylococci* and *Enterococci*, commensal microorganisms of the invention may be modified to lack such antibiotic resistance markers when designated for use in the clinic. In this case, constructs of the invention are stably integrated into the chromosome of a commensal microorganism, so that a resistance marker is not required. A resistance marker that is used to select a stable transformant can be removed after the stable transformant is obtained by a variety of conventional genetic methods. Alternatively, a construct lacking a resistance marker can be introduced into the chromosome by homologous recombination.

Methods for inserting a sequence of interest into a bacterial genome in a stable fashion are conventional. For example, a number of bacteriophage vectors have been developed for use in different bacteria. A bacteriophage vector based on the temperate bacteriophage phi adh can be used (see, e.g., Raya et al. (1992) *J. Bacteriol.* 174, 5584-5592 and Fremaux et al. (1993) *Gene* 125, 61-66). This vector undergoes site-specific integration into the host chromosome at defined phage (attP) and bacterial (attB) attachment sites. Similarly, *Lactobacillus*-specific bacteriophage can be used to transduce vectors or other polynucleotides into the *Lactobacillus* chromosome. *Lactobacillus*-specific phage include mv4 (Auvray et al. (1997) *J. Bacteriol.*, 179, 1837-1845), phi adh (Fremaux et al. (1993) Gene 126, 61-66), phi gle (Kakikawa et al. (1996) *Gene* 175, 157-165, and those belonging to Bradley's groups A or B in vaginal *lactobacillus* isolates (Kilic et al. (2001) *Clin. Diagn. Lab. Immunol.* 8, 31-39).

A commensal bacterium of the invention can be used to treat and/or prevent conditions (e.g., diseases) mediated by a pathogen. It can be used to inhibit infectivity by, and/or a pathogenic activity of, a pathogen. As used herein, the singular forms "a," "an," and "the" include plural referents unless the context clearly dictates otherwise. For example, "a" pathogenic activity, as used above, means one or more pathogenic activities. Among the pathogenic activities that can be inhibited are, e.g., any feature in the life cycle of the pathogen following its initial infection of the host, which allows the pathogen to elicit a detrimental (pathogenic) effect, or the resulting pathologic effects of that infection. Initial infection, or infectivity, by a pathogen includes binding of the pathogen to the host and/or its entry into the host. For enveloped viruses such as HIV, fusion of the virus to the host is included. A commensal bacterium of the invention can, e.g., prevent, inhibit, stabilize, and/or reverse infectivity and/or a pathogenic activity of a pathogen, and/or can regulate or modulate the susceptibility of a cell or tissue to infection by the pathogen.

One aspect of the invention is a method for inhibiting infection by, or a pathogenic activity of, a pathogen (e.g., inhibiting HIV infection) in vitro or in vivo, comprising contacting the pathogen with an effective amount of a commensal bacterium of the invention which secretes a recombinant antimicrobial polypeptide. Such "contacting," as used herein, either in the context of in vitro or in vivo methods, need not involve direct contact of a pathogen with a bacterium of the invention. For example, the bacterium may be at a distance from the pathogen, and an antimicrobial polypeptide secreted by the bacterium may act on the pathogen. Exemplary methods for performing this method are illustrated in the Examples.

Another aspect of the invention is a method for inhibiting infection by, or a pathogenic activity of, a pathogen (e.g., inhibiting HIV infectivity) in a subject (e.g., a patient) in need of such treatment, comprising administering to the subject an effective amount of a commensal bacterium of the invention which secretes an effective amount of a recombinant antimicrobial polypeptide. Another aspect of the invention is a method for treating a patient infected by, or subject to infection by, a pathogen, or for preventing the spread of a pathogen (such as a viral pathogen, particularly HIV) from an infected patient to others, comprising administering to the patient an effective amount of a commensal bacterium of the invention, under conditions effective for the antimicrobial agent secreted by the commensal microorganism to inhibit infectivity by, or a pathogenic activity of, a pathogen of interest.

The hosts (or targets) for administration and colonization by the genetically altered bacteria include: uninfected individuals who are at risk for infection by the pathogen of interest; individuals already infected with the pathogen of interest; various animals infected by or subject to infection by a pathogen, e.g., a mammal, such as an experimental animal, a farm animal, pet, or the like. In preferred embodiments, the animal is a primate, most preferably a human.

The microorganism can be administered to a subject using any of a variety of routes of administration, which will be evident to the skilled worker. Preferably, the microorganism is administered through the oral cavity, or is applied directly to the rectum or the vagina, using conventional methods. Optionally, antibiotic pretreatment of the subject can be used to pre-clear the mucosal surface of resident bacteria prior to introduction of the bacteria of the invention into the rectum, vagina or gastrointestinal tract. See, e.g., Freter et al. (1983) *Infect. Immun.* 39, 686-703 and Example I herein. Antibiotics can be provided orally or can be applied directly, e.g. to the vagina or rectum.

Certain agents that do not irritate mucosal epithelial cells may also be added to a unit dose of the bacteria in capsules or tablets to aid in colonization. Many bacteria on mucosal surfaces secrete capsular materials that coalesce to form a biofilm that covers the entire mucosal surface. It may be beneficial to add an enzyme that digests this biofilm material to promote penetration of the engineered bacteria into the biofilm for more successful colonization. The enzymes include DNAses, peptidases, collagenases, hyaluronidases, and other carbohydrate degrading enzymes. Antibiotics to which the engineered bacteria itself is not susceptible may also be added to decrease the number of resident bacteria on the mucosal surface in order to make room for the engineered bacteria.

Delivery of engineered bacteria to a desired mucosal surface depends on the accessibility of the area and the local conditions. For example, engineered bacteria may be placed in a pharmaceutically acceptable solution, such as a saline solution, or in a foam for delivery onto the vaginal or rectal mucosa. Foams can include, e.g., one or more hydrophobically modified polysaccharides such as cellulosics and chitosans. Cellulosics include, for example, hydroxyethyl cellulose, hydroxypropyl cellulose, methyl cellulose, hydroxypropylmethyl cellulose, hydroxyethyl methyl cellulose, and the like. Chitosans include, for example, the following chitosan salts; chitosan lactate, chitosan salicylate, chitosan pyrrolidone carboxylate, chitosan itaconate, chitosan niacinate, chitosan formate, chitosan acetate, chitosan gallate, chitosan glutamate, chitosan maleate, chitosan aspartate, chitosan glycolate and quaternary amine substituted chitosan and salts thereof, and the like. Foam can also include other components such as water, ethyl alcohol, isopropyl alcohol, glycerin, glycerol, propylene glycol, and sorbitol. Spermicides are optionally included in the bacterial composition. Further examples of foams and foam delivery vehicles are described in, e.g., U.S. Pat. Nos. 5,595,980 and 4,922,928.

Alternatively, the bacteria can be delivered as a suppository or pessary. See, e.g., U.S. Pat. No. 4,322,399. In some embodiments, the bacteria of the invention are prepared in a preservation matrix such as described in U.S. Pat. No. 6,468,526 and are delivered in a dissolvable element made of dissolvable polymer material and/or complex carbohydrate material selected for dissolving properties, such that it remains in substantially solid form before use, and dissolves due to human body temperatures and moisture during use to release the agent material in a desired timed release and dosage. See, e.g., U.S. Pat. No. 5,529,782. The bacteria can also be delivered in vaginal foam or a sponge delivery vehicle such as described in U.S. Pat. No. 4,693,705.

In one embodiment, the bacteria are administered orally, e.g. using a solution of about 0.16M sodium bicarbonate (pH about 8.5) to pre-gavage the subjects and to deliver the bacteria to neutralize the acidic environment of the stomach.

In one embodiment, a commensal bacterium of the invention is administered to a subject by coating, at least in part, a biologically compatible prosthetic device or dildo-like device with the bacterium, and then inserting the coated device into the subject. The biologically compatible device may comprise polymers such as fluorinated ethylene propylene, sulfonated polystyrene, polystyrene, or polyethylene terephthalate, or glass. The device may be, e.g., a catheter such as a urinary or peritoneal catheter, an IUD, or another intravaginal, intrauterine, or intraurethral device. In another embodiment, the device is a condom. In another embodiment, the device is a dildo-like device (e.g., a dildo comprising a small camera at one end, which allows one to follow the administration of the substance). Alternatively, if desired, the device (e.g., a relatively long term device, such as an IUD) can be coated in vivo by administering the commensal bacterium prior to insertion of the device, and allowing an indigenous protective flora to be formed on the device.

The particular mode of administration and the dosage regimen will be selected by the attending clinician, taking into account the particulars of the case (e.g., the subject, the degree of the infection, etc.). Treatment may involve yearly, monthly, daily or multi-daily doses, over a period of a few days to months, or even years. Even less frequent treatments can be used if the commensal organism remains stably associated with the mucosa and continues to secrete the antimicrobial polypeptide for an extended period of time.

The dosage form of a pharmaceutical composition will be determined by the mode of administration chosen. For example, topical and oral formulations can be employed. Topical preparations can include creams, ointments, sprays and the like. Oral formulations may be liquid (e.g., syrups, solutions or suspensions), or solid (e.g., powders, pills, tablets, or capsules). Sprays or drops, such as oral sprays or drops, are also included. For solid compositions (e.g., lyophilized bacteria), conventional non-toxic solid carriers can include pharmaceutical grades of mannitol, lactose, starch, or magnesium stearate. In as preferred application, live bacteria are lyophilized and placed in an enteric-coated capsule, which allows the bacteria not to be released until they have passed through the acidic stomach and reached the more alkaline colon. Actual methods of preparing suitable dosage forms are known, or will be apparent, to those skilled in the art.

Effective dosages of the inhibitory commensal organisms of the invention will be evident to the skilled worker. The exact amount (effective dose) of the agent will vary from subject to subject, depending on, i.a., the species, age, weight and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g., *The Pharmacological Basis of Therapeutics*, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. A therapeutic dose can also be selected by analogy to dosages for comparable therapeutic agents. In general, normal dosage amounts may vary from about $10^8$ bacteria to $10^{11}$ bacteria per person per 1 to 30 days. For example, a daily dose of about $10^9$ to $10^{10}$ *E. coli* Nissle 1917 is typically used for therapy of gastrointestinal complaints. A dose of $10^8$ lactobacilli can be used to restore the normal urogenital flora. See, e.g., Reid et al. (2001) *FEMS Immuno. Med. Microbiol.* 32, 37-41.

In some embodiments, applications of engineered bacteria to a mucosal surface will need to be repeated on a regular basis; optimal dosing intervals are routine to determine, but will vary with different mucosal environments and bacterial strains. The dosing intervals can vary, e.g., from once daily to once every 2-4 weeks. In a most preferred embodiment, the bacteria need be delivered very infrequently (e.g., only once year).

A commensal microorganism of the invention can be formulated as pharmaceutical composition, which comprises the commensal microorganism (e.g., a therapeutically effective amount of the commensal microorganism) and a pharmaceutically acceptable carrier, using conventional components and methodologies. "Therapeutic" compositions and compositions in a "therapeutically effective amount" are compositions that can elicit at least a detectable amount of inhibition or amelioration of infection by, or a pathogenic activity of, a pathogen.

Such pharmaceutical compositions are normally formulated with a solid or liquid carrier, depending upon the particular mode of administration chosen. The pharmaceutically acceptable carriers useful in this disclosure are conventional. Pharmaceutically and physiologically acceptable fluid vehicles, such as water, physiological saline, other balanced salt solutions, aqueous dextrose, glycerol or the like, may be employed. Excipients that can be included are, for instance, other proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate.

The present disclosure also includes combinations of agents of the commensal microorganisms of the invention with one another, and/or with one or more other agents useful in the treatment of a pathogenic infection. For example, commensal microorganisms of the invention may be administered in combination with effective doses of other anti-pathogenic agents, such as an antiretroviral drug. The term "administration in combination" refers to both concurrent and sequential administration of the active agents. The combination therapies are of course not limited to the agents provided herein, but include any composition for the treatment of pathological infections.

Another aspect of the invention is a kit for carrying out any of the methods of the invention. For example, one embodiment is a kit for inhibiting an infection by a pathogen, comprising an effective amount of amount of an inhibitory commensal bacterium of the invention and, optionally, (e.g., if the infection is in a subject in vivo) means for storing or packaging the inhibitory commensal bacterium, or for administering it to a subject.

The components of the kit will vary according to which method is being performed. Optionally, the kits comprise instructions for performing the method. Kits of the invention may further comprise a support on which a cell can be propagated (e.g., a culture vessel). Other optional elements of a kit of the invention include suitable buffers, media components, or the like; containers; or packaging materials. The reagents of the kit may be in containers in which the reagents are stable, e.g., in lyophilized form or stabilized liquids. The reagents may also be in single use form, e.g., in single dosage form for use as therapeutics.

In the foregoing and in the following examples, all temperatures are set forth in uncorrected degrees Celsius; and, unless otherwise indicated, all parts and percentages are by weight.

EXAMPLES

Example I

Expression of an Anti-HIV Peptide by a Commensal Strain of *E. coli*

A. Experimental Design: Choice of Inhibitory Peptide, Secretion System and Bacterial Strain The inventors engineered *E. coli* commensal strain Nissle 1917 to express an HIV fusion inhibitor peptide fused to the carboxy-terminal secretion signal of the hemolysin A gene (hlyA) and showed that the hybrid polypeptide secreted into the culture medium can block HIV infection. Moreover the genetically modified bacteria were capable of colonizing the gastrointestinal tract and the vagina of an experimental animal, the mouse.

Figure 1B:
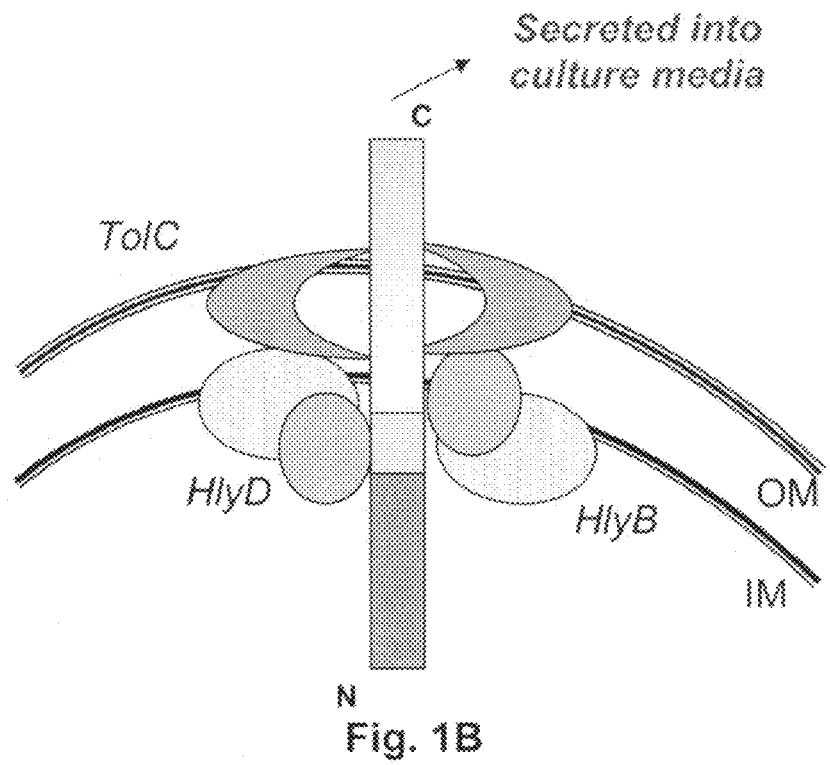
FIG. 1B illustrates the roles of the HlyB, HlyD, and TolC proteins in the secretion of the antimicrobial peptides into the culture media.

As an HIV blocker, a 52 amino acid peptide comprising 47 amino acids from the C-terminal region of gp41 and 5 amino acids added to allow cloning into the expression vector—C52—was chosen. For a further description of C52, see Root et al. (2003) *Proc Natl Acad Sci USA* 100, 5016-5021 and discussions elsewhere herein. The C52 peptide coding sequences were cloned into a high copy number, ampicillin-resistant expression vector containing the E-tag epitope and the final 218 amino acids from the C-terminal secretion signal sequence of hlyA (Fernandez et al. (2000) *Appl Environ Microbiol* 66, 5024-9). Subsequently, the hlyA secretion signal sequence was further truncated to either 103 or 53 amino acids. The structures of the recombinant genes are shown in FIG. 1. The sequences of the recombinant antimicrobial polypeptides encoded by these constructs are:

C52-HlyA218

```
                                            (SEQ ID NO: 6)
MGGHTTWMEWDREINNYTSLIHSLIEESQNQQEKNEQELLELDKWASLW

NWFPGGAPVPYPDPLEPAGENNSLAKNVLSGGKGNDKLYGSEGADLLDG

GEGNDLLKGGYGNDIYRYLSGYGHHIIDDEGGKDDKLSLADIDFRDVAF

KREGNDLIMYKAEGNVLSIGHKNGITFKNWFEKESDDLSNHQIEQIFDK

DGRVITPDSLKKAFEYQQSNNKVSYVYGHDASTYGSQDNLNPLINEISK

IISAAGNFDVKEERSAASLLQLSGNASDFSYGRNSITLTASA;
```

C52-HlyA103

```
                                            (SEQ ID NO: 7)
MGGHTTWMEWDREINNYTSLIHSLIEESQNQQEKNEQELLELDKWASLW

NWFPGGAPVPYPDPLEPAGENLSNHQIEQIFDKDGRVITPDSLKKAFEY

QQSNNKVSYVYGHDASTYGSQDNLNPLINEISKIISAAGNFDVKEERSA

ASLLQLSGNASDFSYGRNSITLTASA;
```

C52-HlyA53

```
                                            (SEQ ID NO: 8)
MGGHTTWMEWDREINNYTSLIHSLIEESQNQQEKNEQELLELDKWASLW

NWFPGGAPVPYPDPLEPAGENLNPLINEISKIISAAGNFDVKEERSAAS

LLQLSGNASDFSYGRNSITLTASA.
```

The HIV C52 fragment was prepared by PCR of DNA from HIV strain NL4-3 with the following two primers:

C52NcoTop:

5' gatggccatgggeggtcacacgacctggatggag3' (SEQ ID NO: 9)

C52XmaBot:

5' attccccgggaaaccaattccacaaacttgc3' (SEQ ID NO: 10)

The PCR product was purified, treated with NcoI and XmaI, and cloned into pEHLYA2-SD cleaved with NcoI and XmaI. Truncations of the HlyA secretion sequence were introduced by oligonucleotide-mediated mutagenesis.

B. Secretion of Anti-HIV Peptides by Nissle 1917

Figure 2A:
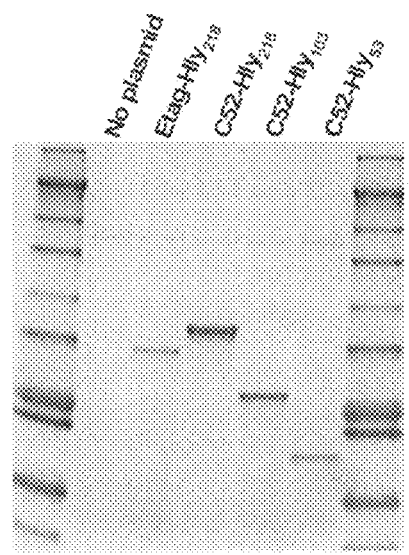
FIG. 2A shows *E. coli* Nissle 1917 that were electroporated with a chloramphenicol resistance plasmid encoding hlyB and hlyD and with an ampicillin resistance plasmid encoding an hlyA fusion peptide. The doubly transformed bacteria were grown in LB for 8 hours and the cell-free supernatants were analyzed by SDS gel electrophoresis and Commassie Blue staining. (1) no hlyA plasmid. (2) Etag-hlyA$_{218}$ (3) C52-hlyA$_{218}$ (4) C52-hlyA$_{103}$ (5) C52-hlyA$_{53}$. The markers on lanes at each end of the gel have approximate molecular weight masses of 188, 98, 62, 49, 38, 28, 17, 14, 6 and 3 kDa.
Figure 2B:
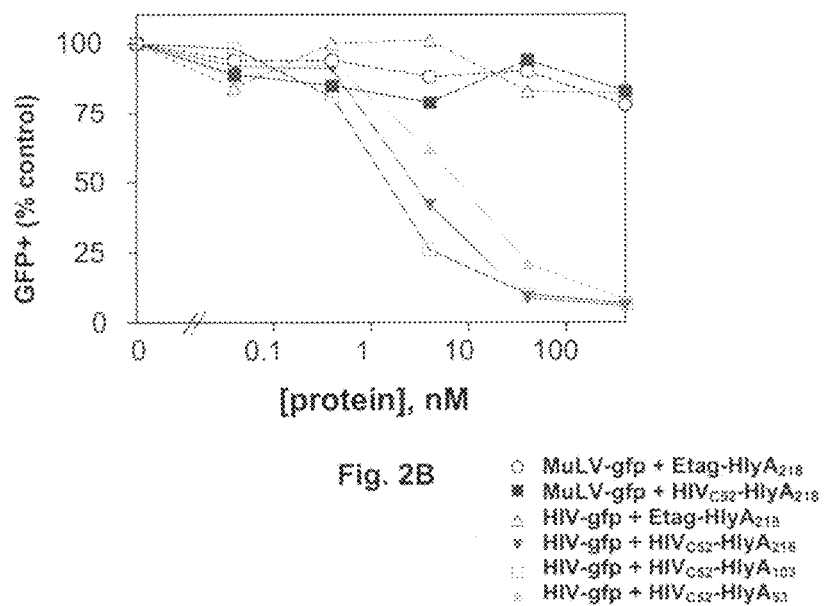
FIG. 2B is a graph which shows PBMC that were incubated with various concentrations of hlyA peptides, infected with an HIV or MuLV-pseudotyped HIV-GFP reporter virus, and assayed for GFP reporter expression by FACS after 2 days. ○ MuLV+Etag-hlyA$_{218}$, ■ MuLV+C52-hlyA$_{218}$; △ HIV+Etag-hlyA$_{218}$, ▼ HIV+C52-hlyA$_{218}$, □ HIV+C52-hlyA$_{103}$, ▲ HIV+C52-hlyA$_{53}$.

The recombinant plasmids were electroporated into *E. coli* Nissle 1917 (obtained from a commercial preparation of the probiotic Mutaflor from Arceypharm, Herdecke, Germany) together with a low copy number chloramphenicol-resistance plasmid that encodes hlyB and hlyD (Fernandez et al. (2000) *Appl Environ Microbiol* 66, 5024-9). Colonies carrying both plasmids were selected on agar plates containing ampicillin and chloramphenicol. These strains were grown in rich medium (Luria broth) to mid log phase, treated with IPTG, and allowed to reach late log phase. The cell-free culture supernatants were then examined by SDS gel electrophoresis. In each case, the C52-hlyA fusion protein was observed as the predominant species secreted into the culture medium (See FIG. 2A). Similar results were obtained in early log phase and in stationary overnight cultures. Moreover, a similar level of expression was observed even in the absence of IPTG induction. The identity of the hybrid proteins was confirmed by Western blotting with an anti-HIV gp41 monoclonal antibody and by complex formation with 5-Helix protein. Similar experiments using C-peptide sequences from $SIV_{mac}239$ led to even higher levels of secreted peptides.

The amount of $C_{52}$-$HlyA_{218}$ peptide secreted by Nissle 1917 was estimated to be 40 mg/liter, representing a peptide concentration of 1.25 µM. Similar expression levels were found in cultures grown to late log phase in the presence or absence of IPTG and in saturated overnight cultures without inducer; this lack of dependence on IPTG was expected due to titration of the available Lac repressor by the high copy number Lac operator. Several other commensal strains of *E. coli* isolated from feces or vagina of normal healthy volunteers (C594.72; C641.72; and C105.72) also expressed the $C_{52}$-$HlyA_{218}$ peptide, but the levels of secreted protein were no greater than or lower than for Nissle 1917.

As shown, fusion peptides having 103 or 53 amino acids from the C-terminus of HlyA were secreted efficiently into the culture medium. By contrast, a fusion peptide having only 43 amino acids from the C-terminus did not show any peptide secretion. These data define the N-terminal boundary of the HlyA secretion signal sequence at 43-53 amino acids upstream of the C terminus of the protein.

One advantage of working with *E. coli* is the extensive knowledge of the cis and trans-acting signals that can be manipulated to increase foreign gene expression. We have previously found that gene aadA1 originating from Tn21 transposon, which confers resistance to aminoglycoside antibiotics, increases the expression of a broad spectrum of cellular proteins in bacteria. Introduction of aadA1 into Nissle 1917 upregulated $C_{52}$-$HlyA_{218}$ peptide expression by 3-fold without any adverse effect on the growth of the bacteria.

C. Inhibition of HIV Infection by Secreted Peptides

The ability of the secreted peptides to block HIV-GFP reporter virus infection was tested in PBMC (peripheral blood mononuclear cells). Various concentrations of the antimicrobial recombinant proteins were incubated with the reporter virus $HIV_{NL4-3}GFP$, in which a GFP (green fluorescent protein) gene allows monitoring of infection by FACS (fluorescence-activated cell sorter). Efficient inhibition was observed for each of the C52-hlyA peptides, but not for the control Etag-hlyA peptide. Inhibition was specific to the HIV envelope glycoprotein as shown by the lack of any effect on pseudovirions encapsidated with MuLV rather then HIV Env (See FIG. 1B). The potency of C52-hlyA$_{218}$ was close to that of 5-Helix, having an $IC_{50}$ value of approximately 1 nM. Similar results were obtained using a $HIV_{JR-CSF}GFP$ reporter virus. Thus the anti-HIV peptides can block infection by both X4 and R5 tropic viruses.

D. Colonization of Mouse Gastrointestinal and Genitourinary Tracts

The ability of the genetically modified *E. coli* Nissle 1917 to colonize the gastrointestinal and genitourinary tracts was investigated using the mouse as a small animal model system. Female mice, strain CD-1 (Charles River laboratories) were administered $5 \times 10^8$ *E. coli* Nissle 1917::C52-HlyA208, either orally (by gavage using 0.2 ml of a 0.16 M sodium bicarbonate solution, pH 8.5) or rectally (by injection using 0.2 ml of a PBS solution). The mice were either treated with no antibiotic, pretreated for one day prior to inoculation with antibiotic (streptomycin sulfate, 2.5 mg/l in drinking water), post-treated for 12 days with antibiotic (ampicillin, 2.4 mg/l in drinking water), or both pre-treated and post-treated with antibiotic. At intervals, feces and vaginal wash samples were collected and assayed for the presence of the recombinant bacteria by plating on agar containing chloramphenicol and ampicillin. In addition, mice were sacrificed at 2 and 7 days post-inoculation, and segments of the gastrointestinal tract and genitourinary tract were dissected and assayed for recombinant bacteria.

Figure 3A:
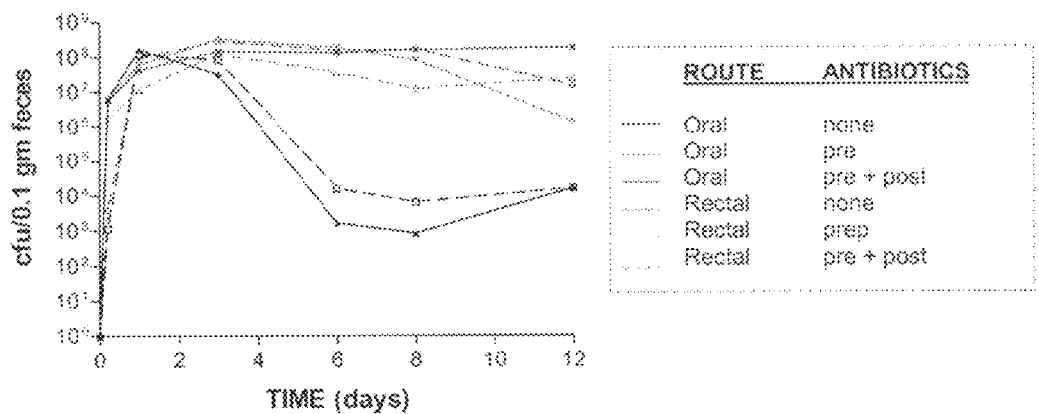
FIG. 3A shows the number of the recombinant bacteria recovered in feces at time intervals.

Substantial colonization of the entire gastrointestinal tract and of the vagina were observed (FIG. 3). The concentrations of bacteria in the feces reached approximately $10^{10}$ per gram, which is as high or higher than the concentration of endogenous *E. coli* in the absence of antibiotic treatment. In animals that received no antibiotic, the number of recombinant bacteria peaked at 1 to 3 days and then declined. However, in mice pre-treated or post-treated with antibiotics, the concentration of bacteria found in feces remained high throughout the 12 day observation period. The maintenance of such a high concentration of bacteria clearly demonstrates that the altered microorganisms are undergoing growth and cell division in the mice.

To investigate the cis and trans-acting signals involved in the maintenance of gastrointestinal tract colonization, mice were given a single treatment with ampicillin, orally administered various bacterial strains, and then maintained without antibiotic for 25 days. Colonization levels of Nissle 1917 expressing $C_{52}$-$HlyA_{218}$ fell more than 10,000-fold over this period (Table 1).

TABLE 1

Effects of cis and trans-acting signals on mouse colonization

| Nissle 1917 | Plasmid | Log cfu/g feces | | Log diff. |
| --- | --- | --- | --- | --- |
| | | Day 1 | Day 25 | |
| wt | pC$_{52}$-HlyA$_{218}$ | 8.35 (0.27) | 3.61 (0.16) | 4.74 |
| aadA1 | pC$_{52}$-HlyA$_{218}$ | 8.42 (0.52) | 4.62 (0.79) | 3.80 |
| wt | Etag-HlyA218 | 7.84 (0.50) | 3.02 (0.27) | 4.81 |
| wt | C52-HlyA103 | 7.98 (0.36) | 5.99 (0.91) | 1.99 |
| wt | C52-HlyA53 | 8.91 (0.13) | 7.00 (0.91) | 1.91 |

Mice were orally administered $5 \times 10^8$ cfu of the indicated strain and maintained without antibiotic. Feces were assayed for Ap$^r$ Cm$^r$ cfu at intervals and the results at day 1 and day 25 are shown as the mean (standard error) of the $\log_{10}$ cfu/g feces #, with errors in parentheses.

This drop in bacterial levels was not simply due to the amount of peptide secreted as shown by the somewhat better retention of bacteria that overproduced the peptide due to the introduction of aadA1 gene. The drop was also not exclusively due to the presence of HIV sequences in the secreted peptide as shown by the poor maintenance of a strain expressing Etag-HlyA$_{218}$. By contrast, the extent of HlyA C-terminal sequences did appear to play an important role as demonstrated by the ability of bacteria expressing the C-terminal deletion mutants $C_{52}$-$HlyA_{103}$ and $C_{52}$-$HlyA_{53}$ to undergo more persistent colonization than $C_{52}$-$HlyA_{218}$, with levels at day 25 more than 100-fold higher than for the full length construct. This conclusion was confirmed by a competitive colonization experiment in which mice were fed an equal mixture of bacteria expressing $C_{52}$-$HlyA_{218}$ and $C_{52}$-$HlyA_{53}$ and subsequently analyzed for the ratio of colonies expressing the different length peptides. At day 1, a slight excess of bacteria expressing the HlyA$_{218}$ construct was excreted, but by day 8 and thereafter only bacteria expressing the short HlyA$_{53}$ construct could be recovered.

To examine the potential of the genetically engineered Nissle for long-term, stable colonization in the absence of antibiotics, mice were administered bacteria expressing a $C_{52}$ peptide both orally and rectally, then maintained on ampicillin for 50 days prior to removal of the antibiotic. The rational for this prolonged initial antibiotic treatment was that it would eliminate much of the competing indigenous microflora while allowing the genetically engineered bacteria to adapt to the nutritional environment of the intestine. In the absence of antibiotics, bacteria expressing $C_{52}$-$HlyA_{218}$ were again eliminated from the mice reaching undetectable levels by 77 days. However, bacteria secreting $C_{52}$-$HlyA_{103}$ and $C_{52}$-$HlyA_{103}$ were maintained in the mice at levels of approximately $10^6$ cfu/g feces for up to 50 days after the removal of drug selection. Bacteria recovered from the mouse feces after prolonged colonization were still capable of secreting high levels of the $C_{52}$ peptides, indicating there was no strong selection against peptide secretion in vivo.

E. In Vivo Growth Patterns and Peptide Secretion.

Figure 3B:
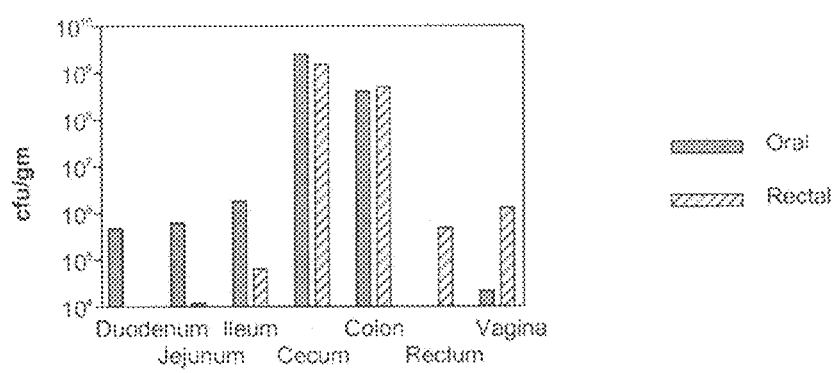
FIG. 3B shows the number of recombinant bacteria recovered from segments of the gastrointestinal tracts and from the vagina after 1 week of colonization.

The distribution of the anti-HIV bacteria in different tissues was examined in mice that has been pre-treated with ampicillin to reduce the endogenous microflora, then orally or rectally administered Nissle 1917 expressing $C_{52}$-$HlyA_{53}$. The highest concentrations of bacteria ($10^8$ to $10^9$ cfu/g) were present in the colon and cecum following both oral and rectal administration (FIG. 3B). Lower levels of bacteria ($10^5$ to $10^6$ cfu/g) were also recovered along the upper intestine including duodenum, jejunum and ileum in mice that were orally inoculated, whereas bacteria were recovered from rectum primarily in mice that were rectally inoculated. Nissle 1917 was also recovered from vagina in approximately one third of rectally inoculated animals. In summary, the commensal bacteria secreting an anti-HIV peptide were capable of colonizing the gastrointestinal and genitourinary tract including the mucosal surfaces at which HIV infection most often occurs.

Tissues from colonized animals were also processed for histopathology and immunohistochemistry. None of the target organs demonstrated any inflammation, necrosis, or other pathology. Detailed examination of the colon revealed the presence of numerous monomorphic, hematoxylin-eosin stained bacterial colonies in animals inoculated with Nissle 1917 expressing $C_{52}$-$HlyA_{53}$ but not in control animals inoculated with PBS. As expected for E. coli, these bacteria were gram negative. The bacterial colonies were present through the lumen, often in close association with the epithelial surface. In some samples, the colon and cecum of Nissle 1917-inoculated animals demonstrated goblet cell hyperplasia and copious mucus secretion into the lumen that was not evident in control PBS-inoculated animals.

To examine peptide secretion, colon samples were subjected to immunohistochemistry using the human monoclonal antibody 2F5, which recognizes an epitope present in the $C_{52}$ peptide. Clear staining was observed through the lumen in samples from animals inoculated with Nissle 1917 expressing $pC_{52}$-$HlyA_{53}$, but not in control samples processed without antibody or from animals expressing control Etag peptide.

Example II

Efficacy Tests, Using Rhesus Macaques

A. Experimental Design: Choice of Bacteria, Test Animals, and Challenge Virus.

The inventor used macaques to demonstrate that a commensal strain of E. coli expressing an HIV fusion inhibitor peptide can colonize the gastrointestinal tract of a primate and that the genetically modified bacteria inhibit infection by an HIV-SIV hybrid virus. The bacteria used for this experiment were E. coli Nissle 1917 expressing C52-HlyA hybrid peptides because the previous data showed that these organisms can secrete high levels of biologically active peptide and can efficiently colonize mucosal surfaces of the gastrointestinal tract (see, l e.g., Example I). The test animals were rhesus macaque of Chinese origin, which were selected because they are a well-studied nonhuman primate model for immunodeficiency virus infection and pathogenesis. The challenge virus was SHIV162p3, an HIV-SIV hybrid virus. This strain was chosen because (i) it uses the same envelope protein as HIV and is therefore a suitable test target for HIV-specific peptides; (ii) it uses the same replication machinery as SIV and therefore can grow and cause disease in macaques; (iii) it utilizes the CCR5 coreceptor, which is the same employed in mucosal transmission of HIV in humans; and (iv) it is a well studied model for HIV microbicide research and carefully characterized and tittered viral stocks are available.

B. Colonization of Macaque Gastrointestinal Tract

Sexually mature male and female Rhesus macaques of Chinese origin were used for the colonization and challenge experiments. In the experiment shown in FIG. 4A, the animals were pretreated starting five days prior to inoculation with oral Cefixime and Cephaclor. At two days prior to inoculation the animals were put on a clear liquid diet, and at one day prior to inoculation PEG and Metronidazole were administered to further reduce endogenous microflora. The animals were then inoculated with a mixture of E. coli Nissle 1917 expressing C52-Hly218, C52-Hly103 and C52-HlyA53 both orally and rectally with $10^{10}$ bacteria in 5 ml of PBS every other day for a total of one week. At intervals, feces samples were collected and assayed for the presence of the recombinant bacteria by plating on agar containing chloramphenicol and ampicillin and by PCR of boiled extracts using plasmid and C52-specific primers. Positive colonies were further verified by growth in rich LB broth and analysis of the secreted peptides by SDS-PAGE.

Figure 4A:
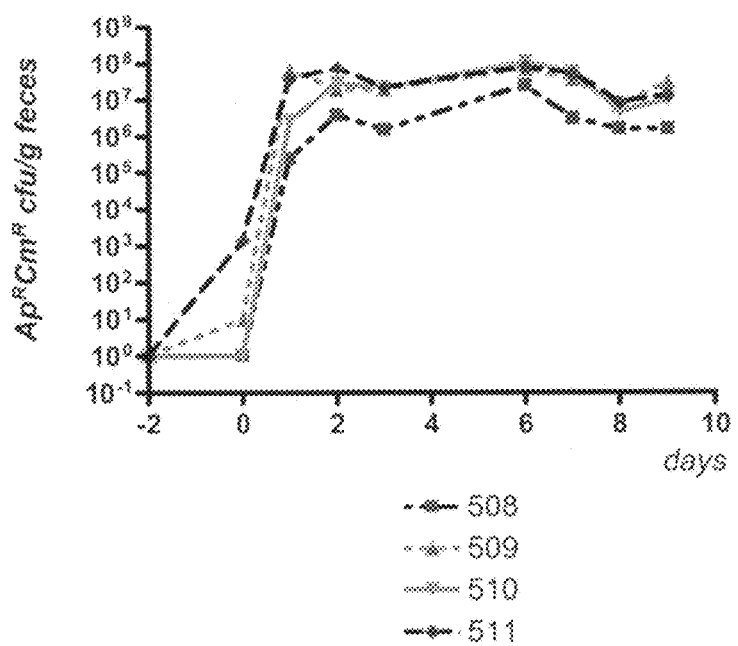
FIG. 4A shows colonization data.

FIG. 4A demonstrates that the recombinant anti-HIV bacteria were capable of colonizing the macaque gastrointestinal tract at levels between $10^6$ and $10^{10}$ colony forming units/gm feces. Furthermore these levels could be maintained as long at 10 days. In additional experiments, colonization was also observed in animals treated with ampicillin rather than Cefixime, Cephaclor and Metronidale, and to a lesser but still significant extent in animals without any antibiotic treatment. The administration of the recombinant bacteria to the macaques had no pathogenic effects as determined by clinical observations, body weight, hematology, and serum clinical chemistry.

Figure 4B:
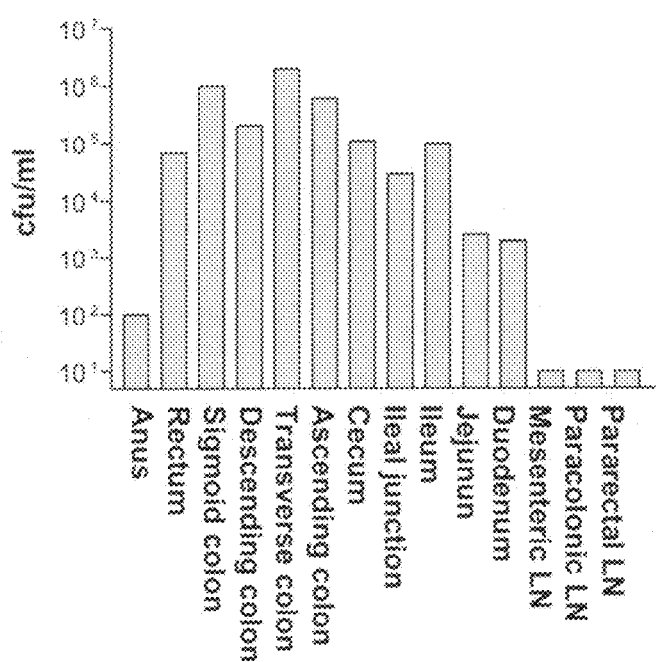
FIG. 4B shows tissue distribution.

To determine the distribution of the bacteria along the intestinal tract, a macaque was orally and rectally administered $10^{10}$ recombinant Nissle then sacrificed one day later for microbiological and histological analysis of tissue. FIG. 4B shows that the highest concentrations of bacteria were present in the colon, cecum and rectum. Somewhat lower but still significant levels of bacteria were also recovered along the upper intestine including duodenum, jejunum, ileum, and the ileal junction. Nissle 1917 was also recovered from anus whereas all tested lymphatic tissues were negative. Microscopic examination revealed heavy concentrations of bacteria through the gastrointestinal tract with no indication of experimentally caused inflammation, necrosis or other pathology.

C. Efficacy Testing.

Figure 5A:
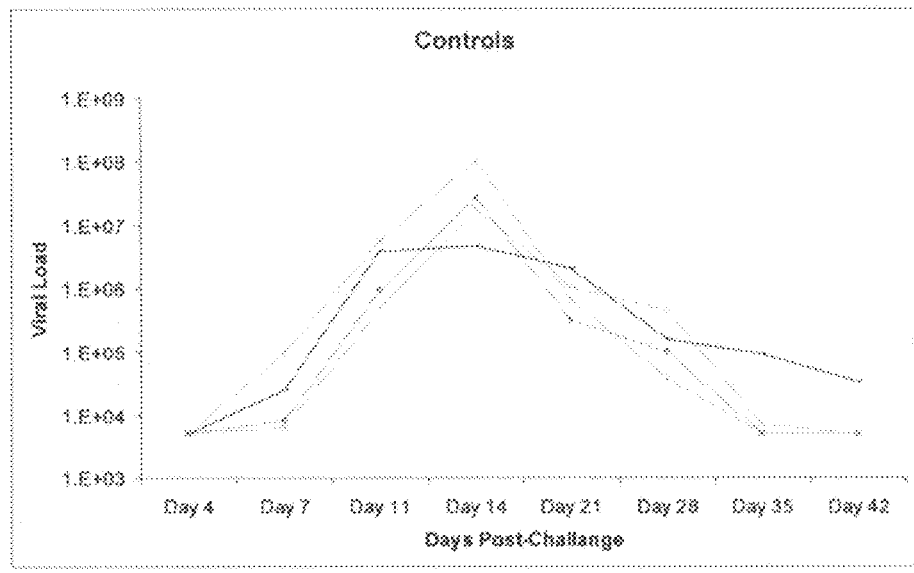
FIG. 5A shows 4 control animals which did not receive the bacteria; all four animals were infected (100% infected); none was protected against viral infection.
Figure 5B:
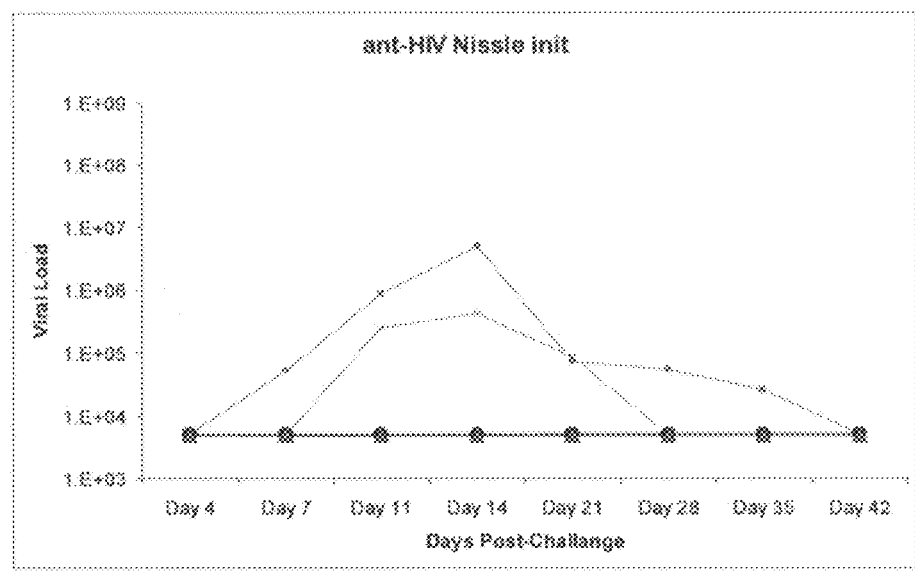
FIG. 5B shows 4 animals that were inoculated with the bacteria. Two of the four animals were protected against viral infection.

Four macaques were colonized with the anti-HIV Nissle 1917 as above, then on day 3 challenged with SHIV162p3, a pathogenic HIV-SIV hybrid that resembles most naturally transmitted HIV-1 strains by using CCR5 as coreceptor. The dose used in this study (1 ml of a 1:10 dilution of a tittered stock virus) gave 100% infection in control animals (FIG. 5A). By contrast, among the animals colonized with anti-HIV Nissle, two were completely protected against viral challenge as determined both by plasma viral RNA measurements (FIG.

5B) and antibody measurements (not shown). Two of the experimental animals were infected, but the viral load levels were on average approximately 10-fold lower than in the control animals. This result suggests that the *E. coli*-based microbicide is capable of protecting roughly 50% of animals against rectal HIV challenge.

In further studies, rhesus macaques of Indian or Chinese origin are used for efficacy tests of bacteria expressing HIVC52-HlyA, SIVC52-HlyA, T1249, and/or other effective HIV-inhibiting peptides, or combinations thereof. Initially, animals are administered a range of doses from about $10^8$ to $10^{11}$ of genetically engineered bacteria by oral gavage, rectal gavage, or intra-vaginal inoculation, with or without pretreatment with ampicillin or other agents as noted above. The extent of colonization and peptide expression are determined by fecal plating assays and/or Western blots. Once animals that stably express the HIV- or SIV-inhibiting and control peptides are obtained, they are challenged with SHIV or SIV by the rectal, vaginal, or oral route. The ability of the bacteria to protect against viral infection is determined by measurements of viral load and CD4 T cells at periodic intervals. The virus stocks used in these studies are first titered and standardized by established procedures used for vaccine candidate testing. It is expected that macaques colonized with bacteria expressing the anti-HIV and anti-SIV peptides will be infected poorly or not at all, whereas macaques colonized with control bacteria will be infected at the normal rate.

REFERENCES

U.S. Pat. Nos. 5,705,160; 5,804,179; 5,821,081; 5,733,540; 6,277,370; 6,365,156; 6,605,286; 6,180,100; U.S. Patent application 20020086020; U.S. Patent application 20030228297; U.S. Patent application 20050003510; Lee et al. (2000) *J Biol Chem* 275, 15809-819.

From the foregoing description, one skilled in the art can easily ascertain the essential characteristics of this invention, and without departing from the spirit and scope thereof, can make changes and modifications of the invention to adapt it to various usage and conditions.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure of all applications, patents and publications, cited above and below and in the figures are hereby incorporated by reference.

I claim:

1. A commensal strain of *E. coli* comprising a polynucleotide that encodes a polypeptide consisting of SEQ.ID.NO:1 or T20, wherein said polypeptide is fused to a hemolysin A secretion signal, and wherein the *E. coli* secretes the polypeptide in an amount effective to inhibit HIV infectivity and/or pathogenicity.

2. The commensal strain of *E. coli* of claim 1, wherein the *E. coli* strain is Nissle 1917.

3. The commensal strain of *E. coli* of claim 1, which can colonize genitourinary mucosa.

4. The commensal strain of *E. coli* of claim 1, which can colonize gastrointestinal mucosa.

5. The commensal strain of *E. coli* of claim 1, wherein expression of the antimicrobial polypeptide is under the control of an expression control sequence that comprises a constitutive promoter.

6. The commensal strain of *E. coli* of claim 5, wherein the expression control sequence comprises a promoter from the *E. coli* lac operon and a translational control sequence from bacteriophage T7.

7. The commensal strain of *E. coli* of claim 1, wherein said polynucleotide is operably linked to an expression control sequence and is stably integrated into the genome of the commensal bacterium.

8. A pharmaceutical composition comprising the commensal strain of *E. coli* of claim 1 and a pharmaceutically acceptable carrier.

9. A method for making the strain of *E. coli* of claim 1, comprising introducing into the strain of *E. coli* the polynucleotide which encodes the polypeptide operably linked to an expression control sequence.

10. The commensal strain of *E. coli* of claim 1, wherein the polypeptide inhibits said HIV infectivity by at least 90% in vitro.

11. The commensal *E. coli* of claim 1, wherein the polypeptide consists of SEQ.ID.NO:1.

12. The commensal *E. coli* of claim 1, wherein the polypeptide is secreted in an amount greater than 10-fold, 20-fold, 50-fold or 75-fold more than an amount known to be needed to inhibit HIV infectivity and/or a pathogenicity.

13. The commensal *E. coli* of claim 1, wherein the polypeptide is T20.

* * * * *

SEQUENCE LISTING

```
<160> NUMBER OF SEQ ID NOS: 10

<210> SEQ ID NO 1
<211> LENGTH: 52
<212> TYPE: PRT
<213> ORGANISM: Human immunodeficiency virus

<400> SEQUENCE: 1

Met Gly Gly His Thr Thr Trp Met Glu Trp Asp Arg Glu Ile Asn Asn
  1               5                  10                  15

Tyr Thr Ser Leu Ile His Ser Leu Ile Glu Glu Ser Gln Asn Gln Gln
             20                  25                  30

Glu Lys Asn Glu Gln Glu Leu Leu Glu Leu Asp Lys Trp Ala Ser Leu
         35                  40                  45

Trp Asn Trp Phe
     50

<210> SEQ ID NO 2
<211> LENGTH: 52
<212> TYPE: PRT
<213> ORGANISM: Simian immunodeficiency virus

<400> SEQUENCE: 2

Met Gly Gly His Thr Thr Trp Gln Glu Trp Glu Arg Lys Val Asp Phe
  1               5                  10                  15

Leu Glu Glu Asn Ile Thr Ala Leu Leu Glu Glu Ala Gln Ile Gln Gln
             20                  25                  30

Glu Lys Asn Met Tyr Glu Leu Gln Lys Leu Asn Ser Trp Asp Val Phe
         35                  40                  45

Gly Asn Trp Phe
     50

<210> SEQ ID NO 3
<211> LENGTH: 217
<212> TYPE: PRT
```

<213> ORGANISM: Escherichia coli

<400> SEQUENCE: 3

Asn Ser Leu Ala Lys Asn Val Leu Ser Gly Gly Lys Gly Asn Asp Lys
1               5                   10                  15
Leu Tyr Gly Ser Glu Gly Ala Asp Leu Leu Asp Gly Gly Glu Gly Asn
                20                  25                  30
Asp Leu Leu Lys Gly Gly Tyr Gly Asn Asp Ile Tyr Arg Tyr Leu Ser
            35                  40                  45
Gly Tyr Gly His His Ile Ile Asp Glu Gly Gly Lys Asp Asp Lys
        50                  55                  60
Leu Ser Leu Ala Asp Ile Asp Phe Arg Asp Val Ala Phe Lys Arg Glu
65                  70                  75                  80
Gly Asn Asp Leu Ile Met Tyr Lys Ala Glu Gly Asn Val Leu Ser Ile
                85                  90                  95
Gly His Lys Asn Gly Ile Thr Phe Lys Asn Trp Phe Glu Lys Glu Ser
            100                 105                 110
Asp Asp Leu Ser Asn His Gln Ile Glu Gln Ile Phe Asp Lys Asp Gly
        115                 120                 125
Arg Val Ile Thr Pro Asp Ser Leu Lys Lys Ala Phe Glu Tyr Gln Gln
130                 135                 140
Ser Asn Asn Lys Val Ser Tyr Val Tyr Gly His Asp Ala Ser Thr Tyr
145                 150                 155                 160
Gly Ser Gln Asp Asn Leu Asn Pro Leu Ile Asn Glu Ile Ser Lys Ile
                165                 170                 175
Ile Ser Ala Ala Gly Asn Phe Asp Val Lys Glu Glu Arg Ser Ala Ala
            180                 185                 190
Ser Leu Leu Gln Leu Ser Gly Asn Ala Ser Asp Phe Ser Tyr Gly Arg
        195                 200                 205
Asn Ser Ile Thr Leu Thr Ala Ser Ala
    210                 215

<210> SEQ ID NO 4
<211> LENGTH: 103
<212> TYPE: PRT
<213> ORGANISM: Escherichia coli

<400> SEQUENCE: 4

Leu Ser Asn His Gln Ile Glu Gln Ile Phe Asp Lys Asp Gly Arg Val
1               5                   10                  15
Ile Thr Pro Asp Ser Leu Lys Lys Ala Phe Glu Tyr Gln Gln Ser Asn
                20                  25                  30
Asn Lys Val Ser Tyr Val Tyr Gly His Asp Ala Ser Thr Tyr Gly Ser
            35                  40                  45
Gln Asp Asn Leu Asn Pro Leu Ile Asn Glu Ile Ser Lys Ile Ile Ser
        50                  55                  60
Ala Ala Gly Asn Phe Asp Val Lys Glu Glu Arg Ser Ala Ala Ser Leu
65                  70                  75                  80
Leu Gln Leu Ser Gly Asn Ala Ser Asp Phe Ser Tyr Gly Arg Asn Ser
                85                  90                  95
Ile Thr Leu Thr Ala Ser Ala
            100

<210> SEQ ID NO 5
<211> LENGTH: 52
<212> TYPE: PRT
<213> ORGANISM: Escherichia coli

```
<400> SEQUENCE: 5

Leu Asn Pro Leu Ile Asn Glu Ile Ser Lys Ile Ile Ser Ala Ala Gly
 1               5                  10                  15

Asn Phe Asp Val Lys Glu Glu Arg Ser Ala Ala Ser Leu Leu Gln Leu
            20                  25                  30

Ser Gly Asn Ala Ser Asp Phe Ser Tyr Gly Arg Asn Ser Ile Thr Leu
         35                  40                  45

Thr Ala Ser Ala
     50

<210> SEQ ID NO 6
<211> LENGTH: 287
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 6

Met Gly Gly His Thr Thr Trp Met Glu Trp Asp Arg Glu Ile Asn Asn
 1               5                  10                  15

Tyr Thr Ser Leu Ile His Ser Leu Ile Glu Glu Ser Gln Asn Gln Gln
            20                  25                  30

Glu Lys Asn Glu Gln Glu Leu Leu Glu Leu Asp Lys Trp Ala Ser Leu
         35                  40                  45

Trp Asn Trp Phe Pro Gly Gly Ala Pro Val Pro Tyr Pro Asp Pro Leu
     50                  55                  60

Glu Pro Ala Gly Glu Asn Asn Ser Leu Ala Lys Asn Val Leu Ser Gly
65                  70                  75                  80

Gly Lys Gly Asn Asp Lys Leu Tyr Gly Ser Glu Gly Ala Asp Leu Leu
                85                  90                  95

Asp Gly Gly Glu Gly Asn Asp Leu Leu Lys Gly Gly Tyr Gly Asn Asp
            100                 105                 110

Ile Tyr Arg Tyr Leu Ser Gly Tyr Gly His His Ile Ile Asp Asp Glu
        115                 120                 125

Gly Gly Lys Asp Asp Lys Leu Ser Leu Ala Asp Ile Asp Phe Arg Asp
    130                 135                 140

Val Ala Phe Lys Arg Glu Gly Asn Asp Leu Ile Met Tyr Lys Ala Glu
145                 150                 155                 160

Gly Asn Val Leu Ser Ile Gly His Lys Asn Gly Ile Thr Phe Lys Asn
                165                 170                 175

Trp Phe Glu Lys Glu Ser Asp Asp Leu Ser Asn His Gln Ile Glu Gln
            180                 185                 190

Ile Phe Asp Lys Asp Gly Arg Val Ile Thr Pro Asp Ser Leu Lys Lys
        195                 200                 205

Ala Phe Glu Tyr Gln Gln Ser Asn Asn Lys Val Ser Tyr Val Tyr Gly
    210                 215                 220

His Asp Ala Ser Thr Tyr Gly Ser Gln Asp Asn Leu Asn Pro Leu Ile
225                 230                 235                 240

Asn Glu Ile Ser Lys Ile Ile Ser Ala Ala Gly Asn Phe Asp Val Lys
                245                 250                 255

Glu Glu Arg Ser Ala Ala Ser Leu Leu Gln Leu Ser Gly Asn Ala Ser
            260                 265                 270

Asp Phe Ser Tyr Gly Arg Asn Ser Ile Thr Leu Thr Ala Ser Ala
        275                 280                 285
```

<210> SEQ ID NO 7
<211> LENGTH: 173
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 7

Met Gly Gly His Thr Thr Trp Met Glu Trp Asp Arg Glu Ile Asn Asn
 1               5                  10                  15

Tyr Thr Ser Leu Ile His Ser Leu Ile Glu Glu Ser Gln Asn Gln Gln
             20                  25                  30

Glu Lys Asn Glu Gln Glu Leu Leu Glu Leu Asp Lys Trp Ala Ser Leu
         35                  40                  45

Trp Asn Trp Phe Pro Gly Gly Ala Pro Val Pro Tyr Pro Asp Pro Leu
 50                  55                  60

Glu Pro Ala Gly Glu Asn Leu Ser Asn His Gln Ile Glu Gln Ile Phe
 65                  70                  75                  80

Asp Lys Asp Gly Arg Val Ile Thr Pro Asp Ser Leu Lys Lys Ala Phe
                 85                  90                  95

Glu Tyr Gln Gln Ser Asn Asn Lys Val Ser Tyr Val Tyr Gly His Asp
            100                 105                 110

Ala Ser Thr Tyr Gly Ser Gln Asp Asn Leu Asn Pro Leu Ile Asn Glu
        115                 120                 125

Ile Ser Lys Ile Ile Ser Ala Ala Gly Asn Phe Asp Val Lys Glu Glu
    130                 135                 140

Arg Ser Ala Ala Ser Leu Leu Gln Leu Ser Gly Asn Ala Ser Asp Phe
145                 150                 155                 160

Ser Tyr Gly Arg Asn Ser Ile Thr Leu Thr Ala Ser Ala
                165                 170

<210> SEQ ID NO 8
<211> LENGTH: 122
<212> TYPE: PRT
<213> ORGANISM: Artificial Sequence
<220> FEATURE:
<223> OTHER INFORMATION: Description of Artificial Sequence: Synthetic
        construct

<400> SEQUENCE: 8

Met Gly Gly His Thr Thr Trp Met Glu Trp Asp Arg Glu Ile Asn Asn
 1               5                  10                  15

Tyr Thr Ser Leu Ile His Ser Leu Ile Glu Glu Ser Gln Asn Gln Gln
             20                  25                  30

Glu Lys Asn Glu Gln Glu Leu Leu Glu Leu Asp Lys Trp Ala Ser Leu
         35                  40                  45

Trp Asn Trp Phe Pro Gly Gly Ala Pro Val Pro Tyr Pro Asp Pro Leu
 50                  55                  60

Glu Pro Ala Gly Glu Asn Leu Asn Pro Leu Ile Asn Glu Ile Ser Lys
 65                  70                  75                  80

Ile Ile Ser Ala Ala Gly Asn Phe Asp Val Lys Glu Glu Arg Ser Ala
                 85                  90                  95

Ala Ser Leu Leu Gln Leu Ser Gly Asn Ala Ser Asp Phe Ser Tyr Gly
            100                 105                 110

Arg Asn Ser Ile Thr Leu Thr Ala Ser Ala
        115                 120

```
<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gatggccatg ggcggtcaca cgacctggat ggag                              34

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
attccccggg aaaccaattc cacaaacttg c                                 31
```